US009897440B2

(12) United States Patent
Gonze et al.

(10) Patent No.: US 9,897,440 B2
(45) Date of Patent: Feb. 20, 2018

(54) METHOD AND SYSTEM FOR DETERMINING AND VERIFYING PLY ORIENTATION OF A COMPOSITE LAMINATE

(71) Applicant: The Boeing Company, Chicago, IL (US)

(72) Inventors: Thomas J. Gonze, Glen Mills, PA (US); James R. Kendall, Mt. Pleasant, SC (US); David C. Jackson, Charleston, SC (US)

(73) Assignee: The Boeing Company, Chicago, IL (US)

( * ) Notice: Subject to any disclaimer, the term of this patent is extended or adjusted under 35 U.S.C. 154(b) by 843 days.

(21) Appl. No.: 14/158,762

(22) Filed: Jan. 17, 2014

(65) Prior Publication Data

US 2016/0102973 A1    Apr. 14, 2016

(51) Int. Cl.
*G01B 11/26*    (2006.01)
*G01B 11/27*    (2006.01)
(Continued)

(52) U.S. Cl.
CPC ......... *G01B 11/272* (2013.01); *G01N 21/898* (2013.01); *B29C 70/30* (2013.01);
(Continued)

(58) Field of Classification Search
CPC ... G01N 2021/8438; G01N 2021/8472; G01N 2291/0231; G01N 2291/2694;
(Continued)

(56) References Cited

U.S. PATENT DOCUMENTS 3,807,868 A    4/1974  Simila
5,127,726 A *  7/1992  Moran .................. G01N 21/88
                                                 250/559.46
(Continued)

FOREIGN PATENT DOCUMENTS

FR    2989621 A1    10/2013

OTHER PUBLICATIONS

European Patent Office Extended European Search Report for Counterpart Patent Application No. EP15151541.8—1504, Applicant The Boeing Company, dated May 20, 2015, 13 pages.
(Continued)

*Primary Examiner* — Tri Ton
*Assistant Examiner* — Rufus Phillips

(57) ABSTRACT

A method for determining and verifying ply orientation of composite laminates includes performing a first scan of a prepared edge of a composite laminate using an off-axis inclined light source directing light at a first acute angle to a first area on the prepared edge to produce a first scanned image; rotating an orientation of the off-axis inclined light source relative to the prepared edge, such that the off-axis inclined light source directs light at a second acute angle symmetrically opposite the first acute angle; and performing a second scan of the prepared edge using the off-axis inclined light source directing light at the second acute angle to the first area on the prepared edge to produce a second scanned image. The method includes comparing the first and second scanned images to determine a ply orientation of each ply, and verifying the ply orientation against a baseline ply orientation.

20 Claims, 9 Drawing Sheets

(51) Int. Cl.
*G01N 21/898* (2006.01)
*G01N 21/84* (2006.01)
*B29C 70/54* (2006.01)
*B29C 70/30* (2006.01)

(52) U.S. Cl.
CPC ...... *B29C 70/54* (2013.01); *G01N 2021/8438* (2013.01); *G01N 2021/8472* (2013.01)

(58) Field of Classification Search
CPC ... G01N 2033/0003; G01N 2033/0096; G01N 2021/8887; G01N 21/55; G01N 2021/8681; G01B 11/26; G01B 11/272
See application file for complete search history.

(56) References Cited

U.S. PATENT DOCUMENTS

| | | | |
|---|---|---|---|
| 5,281,798 A | 1/1994 | Hamm et al. | |
| 5,317,387 A | 5/1994 | Van Hengel et al. | |
| 5,640,244 A | 6/1997 | Hellstrom et al. | |
| 5,917,933 A * | 6/1999 | Klicker | G01N 21/9506 348/125 |
| 7,039,485 B2 * | 5/2006 | Engelbart | B29C 70/386 156/379 |
| 7,197,177 B2 | 3/2007 | Lowe | |
| 9,355,440 B1 * | 5/2016 | Chen | G01N 21/95623 |
| 2004/0032581 A1 * | 2/2004 | Nikoonahad | G01N 21/9501 356/237.2 |
| 2005/0047643 A1 | 3/2005 | Lowe | |
| 2005/0117793 A1 | 6/2005 | Engelbart et al. | |
| 2006/0237156 A1 | 10/2006 | Shakespeare et al. | |
| 2008/0281554 A1 | 11/2008 | Cork et al. | |
| 2014/0210946 A1 * | 7/2014 | Hsiao | H04N 13/0253 348/46 |
| 2015/0099422 A1 * | 4/2015 | Deleris | B29C 73/26 451/2 |

OTHER PUBLICATIONS

F. Gadala-Maria, et al., "Measurement of Fiber Orientation in Short-Fiber Composites Using Digital Image Processing", Polymer Composites, John Wiley & Sons, Hoboken, NJ, US, Apr. 1993, vol. 14, No. 2, pp. 126-131, XP002383082, ISSN: 0272-8397 (p. 130, col. 1, line 1, para. 2-line 3).

Canadian Intellectual Property Office (CIPO) Office Action and Examination Search Report for Counterpart Canadian Patent Application No. 2,872,026, Owner/Applicant The Boeing Company, dated Sep. 19, 2016, 3 pages.

The State Intellectual Property Office (SIPO) of the P.R.C., Notification of First Office Action and Search Report (Chinese Version and English Version), Issued Sep. 19, 2017, for related Chinese Application No. 201510023349.1, The Boeing Company, total of 14 pages.

* cited by examiner

METHOD AND SYSTEM FOR DETERMINING AND VERIFYING PLY ORIENTATION OF A COMPOSITE LAMINATE

BACKGROUND

1) Field of the Disclosure

The disclosure relates generally to methods and systems for analyzing composite structures, and more particularly, to methods and systems for determining and verifying ply orientation of composite laminates used in composite structures, such as aircraft composite structures.

2) Description of Related Art

Composite structures may be used in a wide variety of applications, including in the manufacture of aircraft, spacecraft, rotorcraft, watercraft, automobiles, and other vehicles and structures, due to their high strength-to-weight ratios, corrosion resistance and other favorable properties. In particular, in aircraft construction, composite structures may be used to form the tail sections, wings, fuselage and other component parts of the aircraft.

Composite laminates used to form composite structures may be manufactured by laying up or stacking multiple layers or "plies" together and curing the lay-up. A single layer or ply typically consists of reinforcing fibers in a matrix material. The composite laminates may be stacked with plies of different ply orientations in a defined sequence per design and/or quality requirements to optimize performance, such as load-carrying capacity. For example, the ply orientations may typically include 0° (zero degree) ply orientation, 90° (ninety degree) ply orientation, +45° (plus forty-five degree)/−45° (minus forty-five degree) ply orientation, or another suitable ply orientation. Determining the ply orientation of the composite laminates is important in optimizing composite laminate designs, as well as in complying with composite laminate design and/or quality requirements.

In addition, during the composite laminate manufacturing process, inconsistencies may occur during the lay-up or stacking of the plies, such as, for example, misoriented plies, gaps, overlaps, or other inconsistencies. Methods and systems for determining and verifying ply orientation may be used to analyze the composite laminates for any possible inconsistencies and to ensure that the composite laminates manufactured by the lay-up or stacking process meet the design and/or quality requirements pertaining to ply orientation.

Known methods and systems for determining and verifying ply orientation exist. However, such known methods and systems may require an extensive and time consuming polishing process of an edge or portion of a sample composite laminate to be analyzed. Such polishing process may be needed to obtain sufficient visibility of the fiber orientation of the composite laminate plies. The polishing process may require mounting the sample in an epoxy resin material, or a similar material, so that the sample may be secured in place during the polishing process. Such mounting process may be difficult with large samples that require polishing.

Further, such known methods and systems for determining and verifying ply orientation may require the use of a high magnification microscope, i.e., 100x or greater, to observe the individual fibers of the composite laminate plies of the sample. If the sample to be analyzed is larger than the field of view of the microscope, this may require obtaining multiple images of the composite laminate plies and editing the images together with a known photo editing software to obtain a continuous view of the sample under the microscope. This image preparation process may be time consuming and labor intensive.

Moreover, such known methods and systems for determining and verifying ply orientation may require additional cutting, polishing, and image processing steps to analyze fibers of the sample composite laminate having a +45° (plus forty-five degree) ply orientation and a −45° (minus forty-five degree) ply orientation. To sufficiently distinguish between a +45° (plus forty-five degree) ply orientation and a −45° (minus forty-five degree) ply orientation, a second cut of the sample composite laminate may need to be made and the processes of mounting, polishing, and image processing may need to be performed for both cuts of the +45° (plus forty-five degree) ply orientation and the −45° (minus forty-five degree) ply orientation. The additional work needed to analyze +/−45° (plus/minus forty-five degree) plies may increase the overall time and costs of manufacturing.

Thus, such known methods and systems for determining and verifying ply orientation may be very time consuming, labor intensive, and tedious, and may, in turn, result in increased manufacturing time and costs. For example, a known process for determining and verifying ply orientation that includes mounting, polishing, and image processing steps may take several days to complete.

Accordingly, there is a need in the art for an improved method and system for determining and verifying ply orientation of a composite laminate that provide advantages over known methods and systems.

SUMMARY

Example implementations of the present disclosure provide an improved method and system for determining and verifying ply orientation of a composite laminate to overcome the laborious nature of existing solutions. As discussed in the below detailed description, embodiments of the improved method and system for determining and verifying ply orientation of a composite laminate may provide significant advantages over existing methods and systems.

In an embodiment of the disclosure, there is provided a method for determining and verifying ply orientation of a composite laminate. The method comprises the step of performing a first scan of a prepared edge of the composite laminate using an off-axis inclined light source directing light at a first angle to a first area on the prepared edge to produce a first scanned image. The method further comprises the step of rotating an orientation of the off-axis inclined light source relative to the prepared edge. The method further comprises the step of performing a second scan of the prepared edge using the off-axis inclined light source directing light at a second angle to the first area on the prepared edge to produce a second scanned image.

The method further comprises the step of comparing the first scanned image and the second scanned image to determine a ply orientation of each ply of the composite laminate. The ply orientation is preferably determined based on light source reflections of the off-axis inclined light source. The method further comprises the step of verifying the ply orientation of the composite laminate against a baseline ply orientation of a baseline composite laminate.

In another embodiment of the disclosure, there is provided a method for determining and verifying ply orientation of a composite laminate of an aircraft composite structure. The method comprises the step of preparing an edge of the composite laminate to obtain a prepared edge. The method further comprises the step of performing with a scanning device having at least one off-axis inclined light source a first scan of the prepared edge using the at least one off-axis inclined light source to direct light at a first angle to a first area on the prepared edge to produce a first scanned image. The method further comprises the step of rotating 180 degrees an orientation of the at least one off-axis inclined light source relative to the prepared edge. The method further comprises the step of performing with the scanning device a second scan of the prepared edge using the at least one off-axis inclined light source to direct light at a second angle to the first area on the prepared edge to produce a second scanned image.

The method further comprises the step of transferring the first scanned image and the second scanned image from the scanning device to a processing device for processing. The method further comprises the step of comparing the first scanned image and the second scanned image to determine a ply orientation of each ply of the composite laminate. The ply orientation is preferably determined based on light source reflections of the at least one off-axis inclined light source. The method further comprises the step of preparing a baseline matrix comprising a baseline ply orientation of a baseline composite laminate of the aircraft composite structure. The method further comprises the step of verifying the ply orientation of the composite laminate against the baseline ply orientation of the baseline matrix.

In another embodiment of the disclosure, there is provided a system for determining and verifying ply orientation of a composite laminate. The system comprises a composite laminate that is cured and comprises at least one prepared edge and a plurality of plies, each ply having a ply orientation.

The system further comprises a scanning assembly. The scanning assembly comprises a scanning device having at least one off-axis inclined light source configured to direct light at a first angle to a first area on the prepared edge of the composite laminate to illuminate and capture a first scanned image. The at least one off-axis inclined light source is further configured to direct light at a second angle to the first area on the prepared edge to illuminate and capture a second scanned image. The scanning assembly further comprises a processing device coupled to the scanning device. The processing device is configured to receive and process the first scanned image and the second scanned image from the scanning device. The scanning assembly further comprises a baseline matrix comprising a baseline ply orientation of a baseline composite laminate.

The system provides a ply orientation determination of each ply of the composite laminate based on light source reflections of the at least one off-axis inclined light source and a comparison of the first scanned image and the second scanned image. The system further provides a ply orientation verification of the composite laminate using the baseline matrix.

The features, functions, and advantages that have been discussed can be achieved independently in various embodiments of the disclosure or may be combined in yet other embodiments further details of which can be seen with reference to the following description and drawings.

BRIEF DESCRIPTION OF THE DRAWINGS

The disclosure can be better understood with reference to the following detailed description taken in conjunction with the accompanying drawings which illustrate preferred and exemplary embodiments, but which are not necessarily drawn to scale, wherein.

DETAILED DESCRIPTION

Disclosed embodiments will now be described more fully hereinafter with reference to the accompanying drawings, in which some, but not all of the disclosed embodiments are shown. Indeed, several different embodiments may be provided and should not be construed as limited to the embodiments set forth herein. Rather, these embodiments are provided so that this disclosure will be thorough and will fully convey the scope of the disclosure to those skilled in the art.

Figure 1:
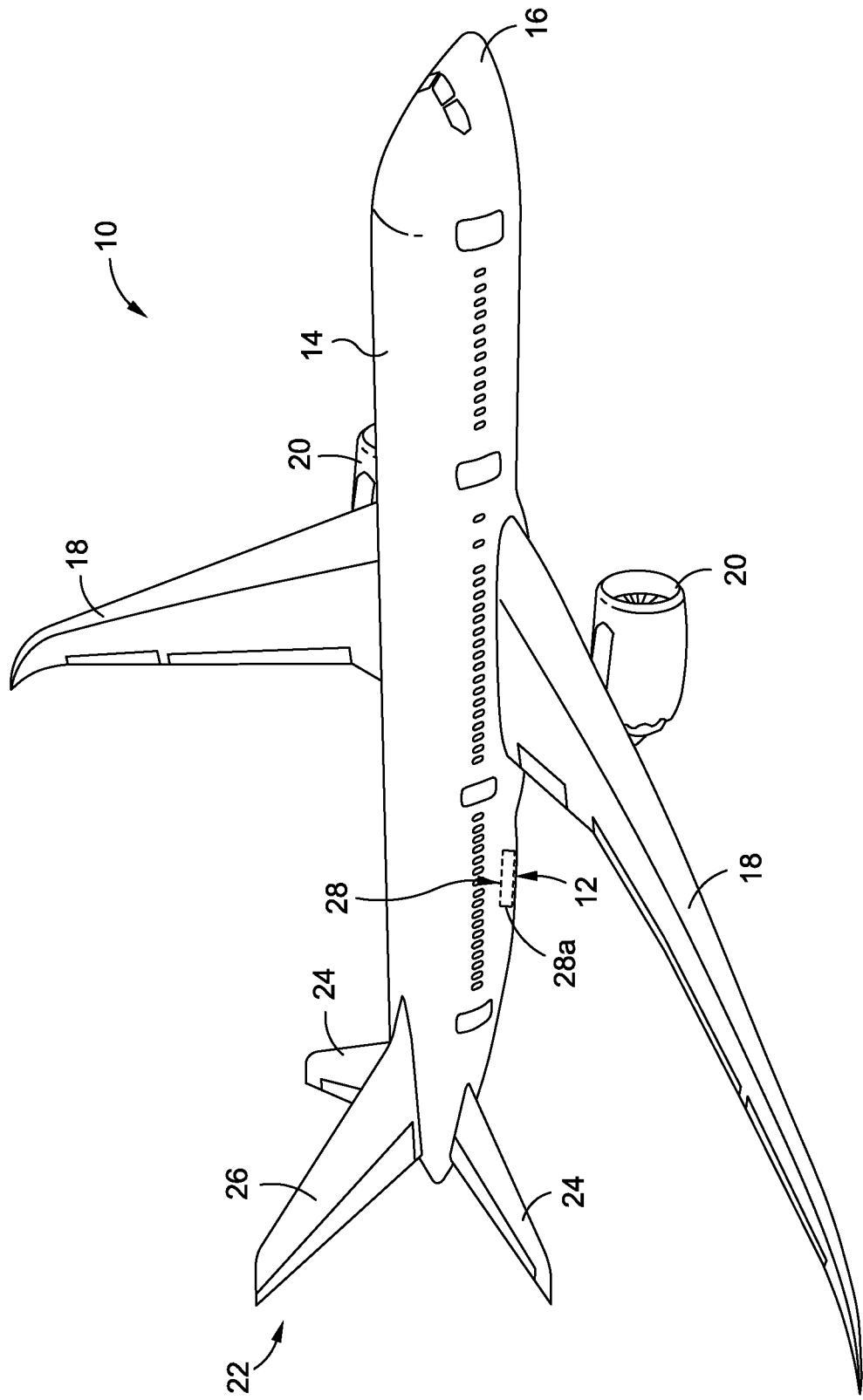
FIG. 1 is an illustration of a perspective view of an aircraft having one or more composite structures that may be scanned and verified using embodiments of a method and a system of the disclosure.

Now referring to the Figures, FIG. 1 is an illustration of a perspective view of an aircraft 10 having one or more composite structures 12. As further shown in FIG. 1, the aircraft 10 comprises a fuselage 14, a nose 16, wings 18, engines 20, and an empennage 22 comprising horizontal stabilizers 24 and a vertical stabilizer 26. As further shown in FIG. 1, the one or more composite structures 12 may comprise a composite laminate 28. Preferably, the composite laminate 28 (see FIG. 1), discussed in further detail below, is cured and is in the form of a fiber-reinforced composite laminate 28a (see FIG. 1).

Embodiments of the disclosure, discussed in detail below, provide a method 66 (see FIG. 4A) for determining and verifying ply orientation of the composite laminate 28 (see FIGS. 1, 5), provide a method 80 (see FIG. 4B) for determining and verifying ply orientation of the composite laminate 28 of the aircraft composite structure 12, and provide a system 90 (see FIG. 5) for determining and verifying ply orientation of the composite laminate 28 (see FIGS. 1, 5).

Figure 2:
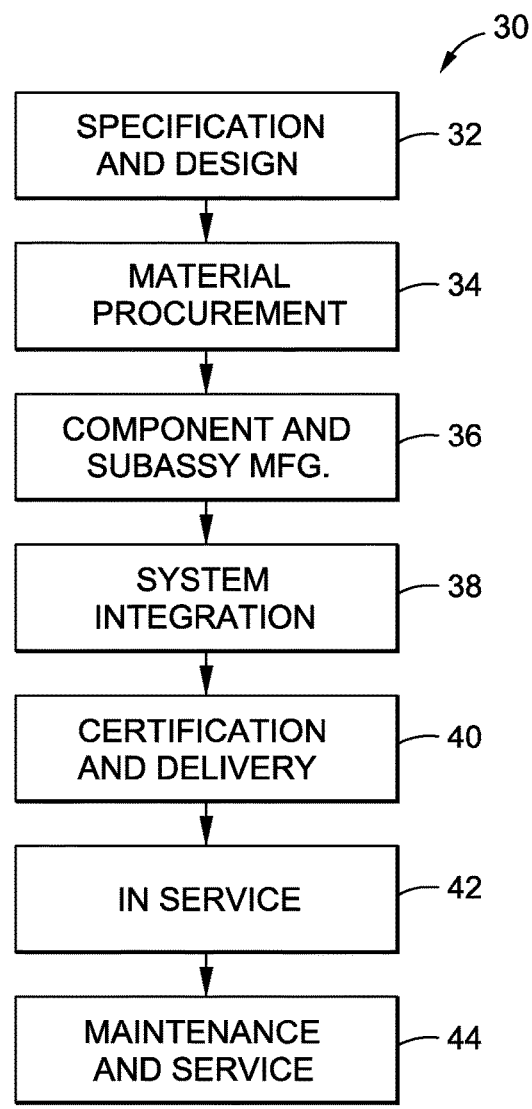
FIG. 2 is an illustration of a flow diagram of an embodiment of an aircraft manufacturing and service method.
Figure 3:
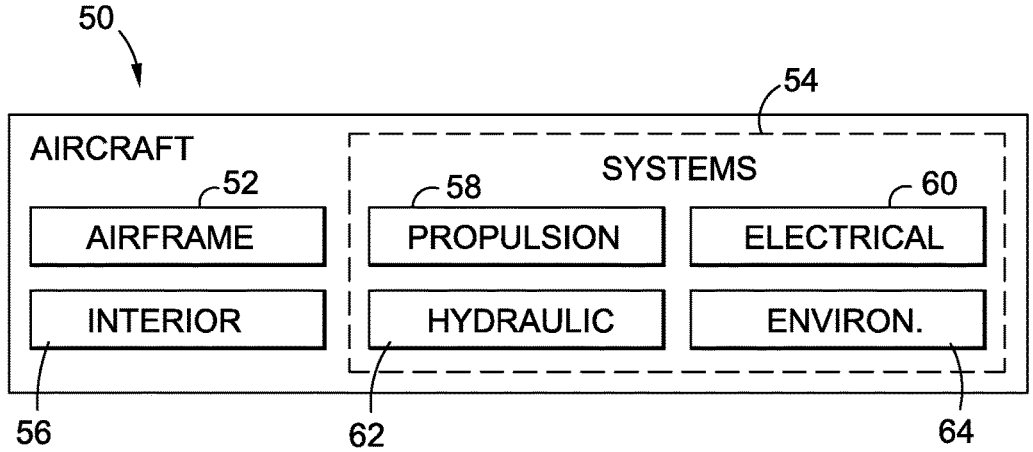
FIG. 3 is an illustration of a functional block diagram of an embodiment of an aircraft.

FIG. 2 is an illustration of a flow diagram of an embodiment of an aircraft manufacturing and service method 30. FIG. 3 is an illustration of a functional block diagram of an embodiment of an aircraft 50. Referring to FIGS. 2-3, embodiments of the disclosure may be described in the context of the aircraft manufacturing and service method 30, as shown in FIG. 2, and the aircraft 50, as shown in FIG. 3. During pre-production, the exemplary aircraft manufacturing and service method 30 (see FIG. 2) may include specification and design 32 (see FIG. 2) of the aircraft 50 (see FIG. 3) and material procurement 34 (see FIG. 2). During manufacturing, component and subassembly manufacturing 36 (see FIG. 2) and system integration 38 (see FIG. 2) of the aircraft 50 (see FIG. 3) takes place. Thereafter, the aircraft 50 (see FIG. 3) may go through certification and delivery 40 (see FIG. 2) in order to be placed in service 42 (see FIG. 2). While in service 42 (see FIG. 2) by a customer, the aircraft 50 (see FIG. 3) may be scheduled for routine maintenance and service 44 (see FIG. 2), which may also include modification, reconfiguration, refurbishment, and other suitable services.

Each of the processes of the aircraft manufacturing and service method 30 (see FIG. 2) may be performed or carried out by a system integrator, a third party, and/or an operator (e.g., a customer). For the purposes of this description, a system integrator may include, without limitation, any number of aircraft manufacturers and major-system subcontractors; a third party may include, without limitation, any number of vendors, subcontractors, and suppliers; and an operator may include an airline, leasing company, military entity, service organization, and other suitable operators.

As shown in FIG. 3, the aircraft 50 produced by the exemplary aircraft manufacturing and service method 30 may include an airframe 52 with a plurality of systems 54 and an interior 56. As further shown in FIG. 3, examples of the systems 54 may include one or more of a propulsion system 58, an electrical system 60, a hydraulic system 62, and an environmental system 64. Any number of other systems may be included. Although an aerospace example is shown, the principles of the disclosure may be applied to other industries, such as the automotive industry.

Methods and systems embodied herein may be employed during any one or more of the stages of the aircraft manufacturing and service method 30 (see FIG. 2). For example, components or subassemblies corresponding to component and subassembly manufacturing 36 (see FIG. 2) may be fabricated or manufactured in a manner similar to components or subassemblies produced while the aircraft 50 (see FIG. 3) is in service 42 (see FIG. 2). Also, one or more apparatus embodiments, method embodiments, or a combination thereof, may be utilized during component and subassembly manufacturing 36 (see FIG. 2) and system integration 38 (see FIG. 2), for example, by substantially expediting assembly of or reducing the cost of the aircraft 50 (see FIG. 3). Similarly, one or more of apparatus embodiments, method embodiments, or a combination thereof, may be utilized while the aircraft 50 (see FIG. 3) is in service 42 (see FIG. 2), for example and without limitation, to maintenance and service 44 (see FIG. 2).

Figure 4A:
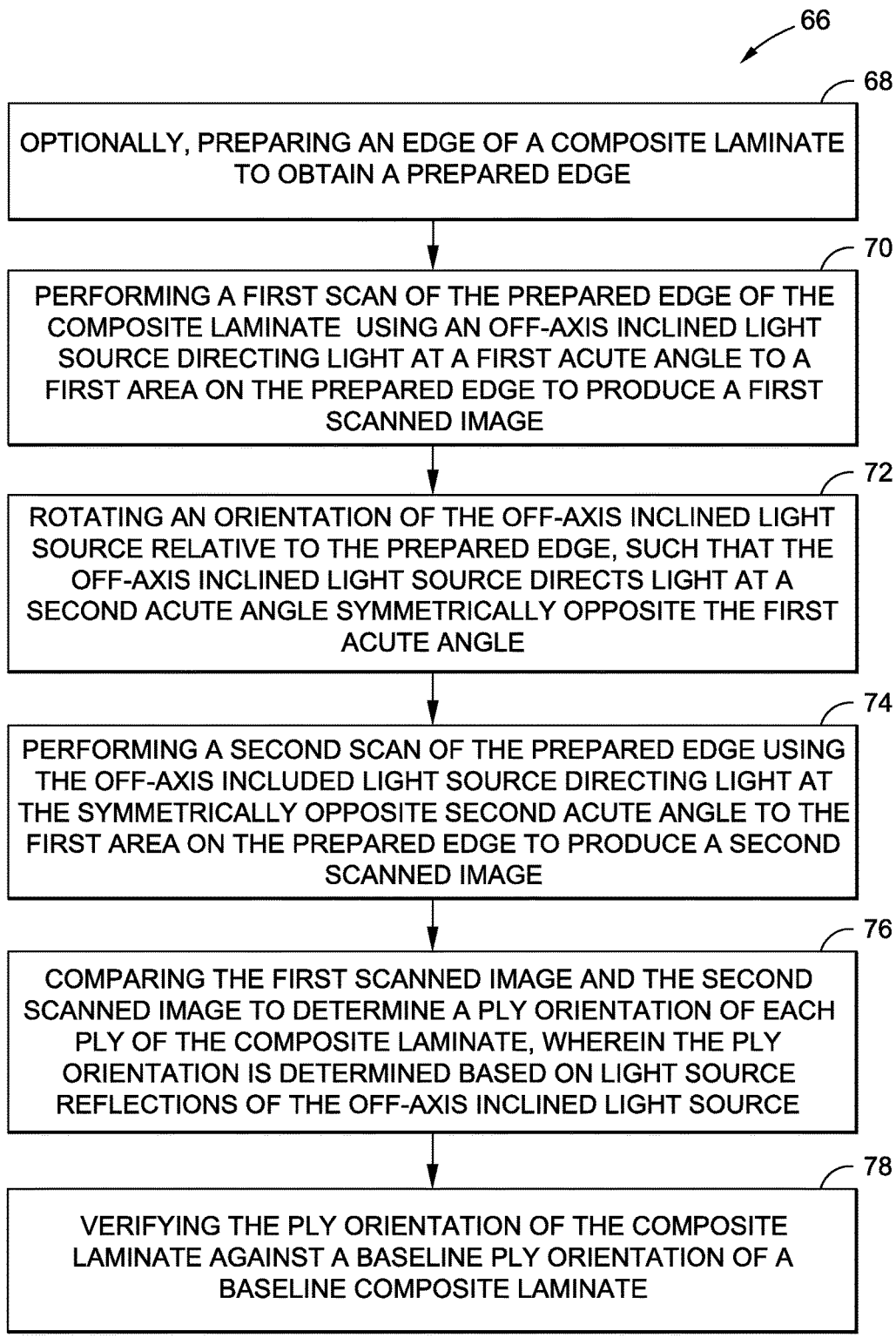
FIG. 4A is an illustration of a flow diagram of one of the embodiments of a method for determining and verifying ply orientation of a composite laminate of the disclosure.
Figure 5:
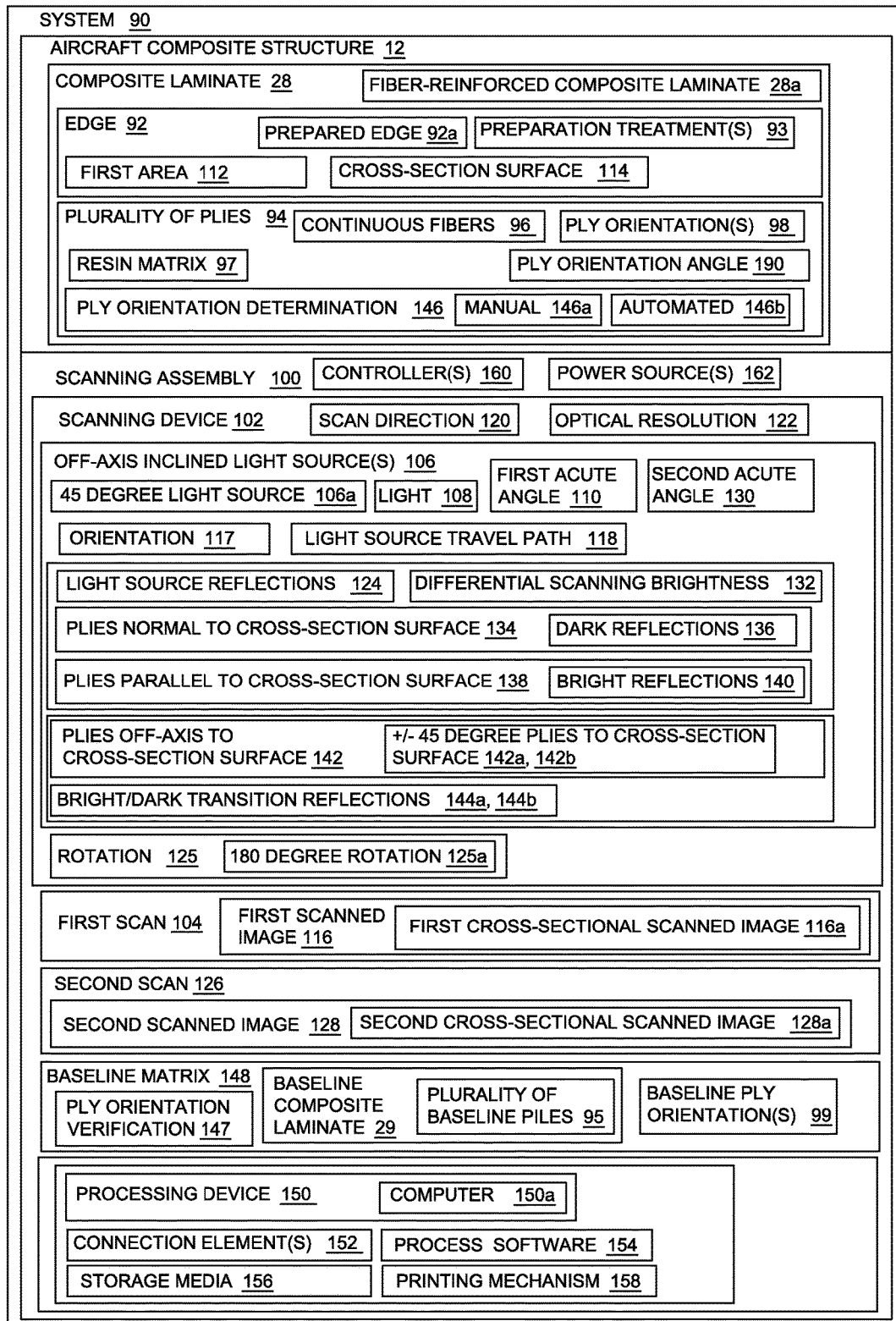
FIG. 5 is an illustration of a functional block diagram of an embodiment of a system for determining and verifying ply orientation of a composite laminate of the disclosure.

Referring to FIG. 4A, in an embodiment of the disclosure, there is provided a method 66 for determining and verifying a ply orientation 98 (see FIG. 5) of the composite laminate 28 (see FIGS. 1, 5). FIG. 4A is an illustration of a flow diagram of one of the embodiments of the method 66 for determining and verifying ply orientation 98 (see FIG. 5) of the composite laminate 28 (see FIG. 5).

Figure 4B:
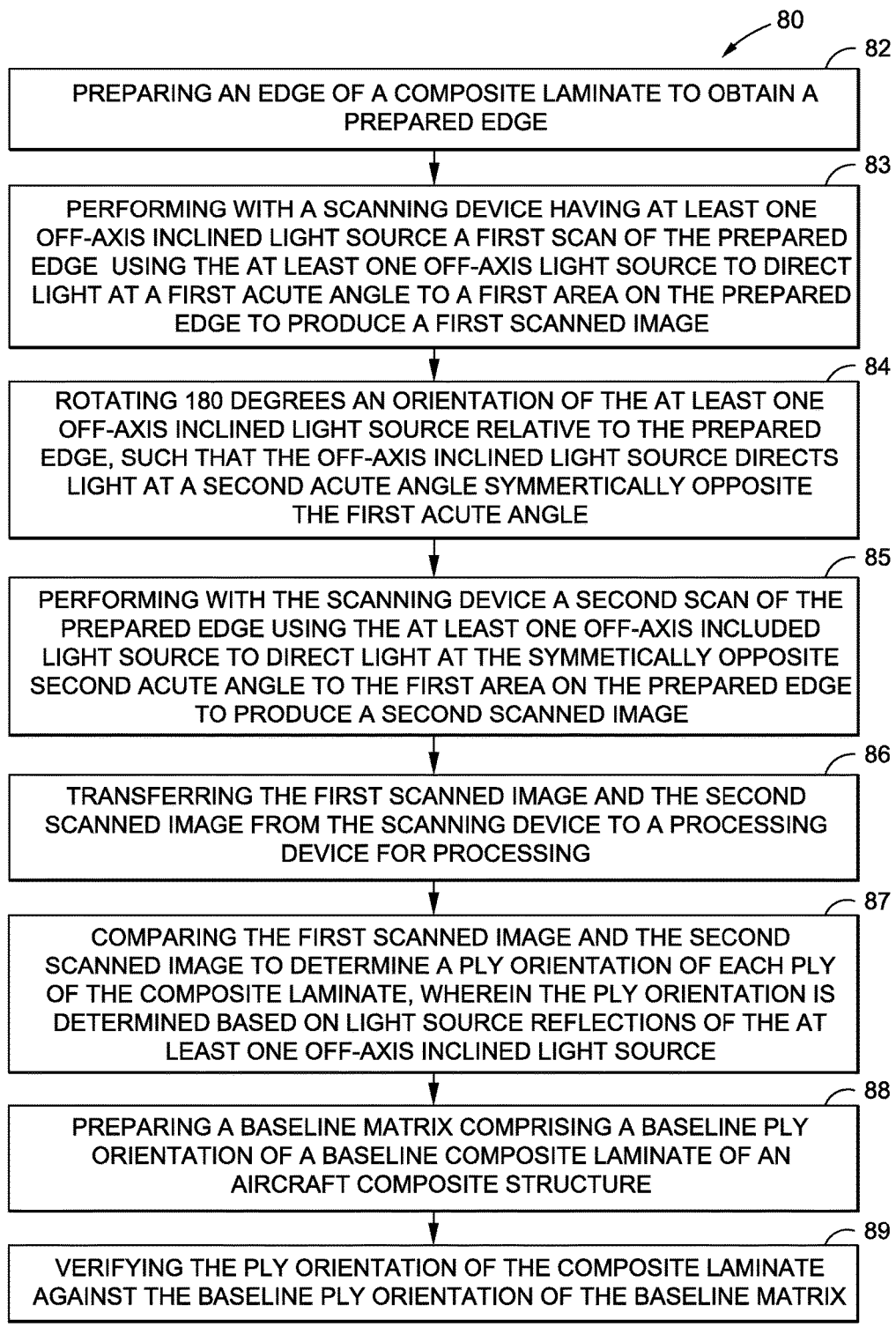
FIG. 4B is an illustration of a flow diagram of one of the embodiments of a method for determining and verifying ply orientation of a composite laminate of an aircraft composite structure of the disclosure.

Referring to FIG. 4B, in another embodiment of the disclosure, there is provided a method 80 for determining and verifying ply orientation 98 (see FIG. 5) of the composite laminate 28 (see FIGS. 1, 5) of the aircraft composite structure 12 (see FIGS. 1, 5). FIG. 4B is an illustration of a flow diagram of one of the embodiments of the method 80 for determining and verifying ply orientation 98 (see FIG. 5) of the composite laminate 28 (see FIG. 5) of the aircraft composite structure 12 (see FIGS. 1, 5).

Referring to FIG. 5, in another embodiment of the disclosure, there is provided a system 90 for determining and verifying ply orientation 98 of the composite laminate 28. FIG. 5 is an illustration of a functional block diagram of an embodiment of the system 90 for determining and verifying ply orientation 98 of the composite laminate 28.

In the below discussion of the method 66 shown in FIG. 4A, reference will be made to various components of the related system 90 of FIG. 5. Similarly, in the below discussion of the method 80 shown in FIG. 4B, reference will be made to the various components of the related system 90 of FIG. 5.

As shown in FIG. 4A, the method 66 comprises optional step 68 of preparing an edge 92 (see FIG. 5) of the composite laminate 28 (see FIG. 5) to obtain a prepared edge 92a (see FIG. 5). During manufacture of the composite laminate 28 (see FIG. 5), one or more edges 92 (see FIG. 5) of the composite laminate 28 (see FIG. 5) may become rough and may require one or more preparation treatments 93 (see FIG. 5), in order to obtain a prepared edge 92a (see FIG. 5) that is smooth or polished prior to undergoing the scanning steps of the method 66 (see FIG. 4A), discussed below. Preferably, the preparation treatments 93 (see FIG. 5) comprise one or more procedures, such as smoothing, polishing, abrading, finishing, cleaning, or another suitable preparation treatment of the edge 92a (see FIG. 5) of the composite laminate 28 (see FIG. 5). The preparation treatments 93 (see FIG. 5) may be performed via a manual process, for example, manually by rubbing the edge 92 (see FIG. 5) with sandpaper or another abrading device, with a polishing or cleaning solution or device, or with another suitable manual preparation treatment. Alternatively, the preparation treatments 93 (see FIG. 5) may be performed via an automated process, or via a combination of manual and automated processes.

The step 68 of preparing the edge 92 (see FIG. 5) may be performed in a short period of time, and preferably, in about ten (10) minutes to thirty (30) minutes, and more preferably, in about ten (10) minutes. This short preparation treatment time for preparing the edge 92 (see FIG. 5) is advantageous, as compared to the mounting and polishing processes required in known methods for determining and verifying ply orientation, which may take hours or days to complete.

The composite laminate 28 (see FIGS. 1, 5) is preferably in the form of a fiber-reinforced composite laminate 28a (see FIGS. 1, 5) comprised of a plurality of plies 94 (see FIG. 5). Preparing the edge 92 (see FIG. 5) of the composite laminate 28 (see FIGS. 1, 5) to obtain the prepared edge 92a (see FIG. 5) preferably facilitates visibility of the plurality of plies 94 (see FIG. 5) at the prepared edge 92a (see FIG. 5), in scanned images of the prepared edge 92a, after the prepared edge 92a has been scanned, as discussed below.

The plurality of plies 94 (see FIG. 5) preferably comprise continuous fibers 96 (see FIG. 5) in a resin matrix material 97 (see FIG. 5). Continuous fibers 96 (see FIG. 5) are preferred over discontinuous or chopped fibers. With continuous fibers 96 (see FIG. 5), there may be few, if any, breaks in the reinforcements, and continuous fibers 96 may provide improved performance properties of the composite laminate 28 (see FIG. 5).

The continuous fibers 96 (see FIG. 5) comprising the plurality of plies 94 (see FIG. 5) preferably comprise reinforcement or high-strength fibers made of one or more materials, such as carbon, glass, fiberglass, graphite, boron, aromatic polyamide, silicon carbide, or another suitable reinforcement or high-strength material. The resin matrix material 97 (see FIG. 5) may comprise polymeric, ceramic, metallic or other matrix materials, such as epoxy, polyester, vinyl ester resins, polyetheretherketone polymer (PEEK), polyetherketoneketone polymer (PEKK), polyimides, bismaleimide, aluminum, titanium, alumina, or another suitable matrix material. As used herein, "cured" means undergoing a full or partial hardening process, with or without heat, for example, the resin matrix material hardening to form a strong, rigid, fiber-reinforced composite laminate.

The plurality of plies 94 (see FIG. 5) of the composite laminate 28 (see FIGS. 1, 5) may comprise a prepreg unidirectional tape, a unidirectional fiber tape, a carbon fiber-reinforced plastic (CFRP) tape, or another suitable tape; a carbon fiber-reinforced plastic (CFRP) fabric, a prepreg fabric, a woven fabric including a woven carbon fiber fabric, or another suitable fabric; a combination of a tape or a fabric thereof; or another suitable composite material.

The composite laminate 28 (see FIG. 5) may be formed of a composite material by any suitable means including, but not limited to, hand lay up, automated lay up, or another suitable forming process. Each ply 94 (see FIG. 5) preferably has a ply orientation 98 (see FIG. 5). The ply orientation 98 (see FIG. 5) may be tailored to any ply direction desired. For example, the ply orientation 98 (see FIG. 5) may include, without limitation, such ply orientations as: 0° (zero degree) ply orientation, where a ply orientation angle 190 (see FIG. 5) of the fiber is 0° (zero degrees) or parallel to a cross-section surface 114 (see FIGS. 5, 6A) of the prepared edge 92a (see FIGS. 5, 6A); 90° (ninety degree) ply orientation, where the ply orientation angle 190 (see FIG. 5) of the fiber is 90° (ninety degrees) or perpendicular or normal to the cross-section surface 114 (see FIGS. 5, 6A) of the prepared edge 92a (see FIGS. 5, 6A); +45° (plus forty-five degree)/−45° (minus forty-five degree) ply orientation, where the ply orientation angle 190 (see FIG. 5) of the fiber is +45° (plus forty-five degrees)/−45° (minus forty-five degrees) to the cross-section surface 114 (see FIGS. 5, 6A) of the prepared edge 92a (see FIG. 5), or another suitable ply orientation.

As used herein, "ply orientation angle" means the angle that the fibers of a ply make with a cross-section surface of a prepared edge of a composite laminate, or alternatively, the angle that the fibers of a ply make with a surface of a scanning device that a sample of the composite laminate is positioned on for image scanning. Further, by way of example, as used herein, "+45° (plus forty-five degrees)" means that a ply is rotated 45° (forty-five degrees) clockwise relative to the orientation of an adjacent ply layer and "−45° (minus forty-five degrees)" means that a ply is rotated 45° (forty-five degrees) counterclockwise relative to the orientation of an adjacent ply layer.

As shown in FIG. 4A, the method 66 further comprises step 70 of performing a first scan 104 (see FIGS. 5, 6A) of the prepared edge 92a (see FIG. 5) of the composite laminate 28 (see FIG. 5). The first scan 104 (see FIG. 5) is preferably performed using an off-axis inclined light source 106 (i.e., a light source that is not perpendicular to the prepared edge 92a as shown in FIG. 5). The off-axis inclined light source 106 (see FIG. 5) preferably directs light 108 (see FIG. 5) at a first acute angle 110 relative to the prepared edge 92a (i.e., an angle that is not perpendicular to the prepared surface as shown in FIG. 5), to direct light 108 to a first area 112 (see FIG. 5) on the prepared edge 92a (see FIG. 5) to produce a first scanned image 116 (see FIG. 5). The off-axis inclined light source 106 (see FIG. 5) illuminates the first area 112 (see FIG. 5) on the prepared edge 92a (see FIG. 5).

As shown in FIG. 4A, the method 66 further comprises step 72 of rotating an orientation 117 (see FIG. 5) of the off-axis inclined light source 106 (see FIG. 5) at a rotation 125 (see FIG. 5) relative to the prepared edge 92a (see FIG. 5) of the composite laminate 28 (see FIG. 5). The step 72 of rotating the orientation 117 (see FIG. 5) of the off-axis inclined light source 106 (see FIG. 5) preferably comprises rotating the orientation 117 (see FIG. 5) of the off-axis inclined light source 106 in a 180 degree rotation 125a (see FIG. 5) relative to the prepared edge 92a (see FIG. 5) of the composite laminate 28 (see FIG. 5).

As shown in FIG. 4A, the method 66 further comprises step 74 of performing a second scan 126 (see FIG. 5) of the prepared edge 92a (see FIG. 5) of the composite laminate 28 (see FIG. 5). The second scan 126 (see FIG. 5) is preferably performed with the orientation of the off-axis inclined light source 106 (see FIG. 5) rotated 180 degrees from that of the first scan. With the orientation of the off-axis inclined light source rotated 180 degrees relative that of the first scan, the off-axis inclined light source 106 (see FIG. 5) preferably directs light 108 (see FIG. 5) at a second acute angle 130 relative to the prepared edge 92a that is symmetrically opposite the first acute angle 110 (see FIG. 5), to direct light at a symmetrically opposite second acute angle 110 to the first area 112 (see FIG. 5) on the prepared edge 92a to produce a second scanned image 128 (see FIG. 5).

The step 70 (see FIG. 4A) of performing the first scan 104 (see FIG. 5) of the prepared edge 92a (see FIG. 5) and the step 74 (see FIG. 4A) of performing the second scan 126 (see FIG. 5) of the prepared edge 92a (see FIG. 5) preferably comprise using a scanning device 102 (see FIG. 5) having a light source 106a (see FIG. 5) oriented at an angle of 45° (forty-five degree) relative to the prepared surface, such that light directed at the first acute angle 110 is about 45° (forty-five degree) relative to the prepared surface and light directed at the second acute angle 130 is about 45° (forty-five degree) relative to the prepared surface and symmetrically opposite the first acute angle 110.

The scanning device 102 (see FIG. 5) is preferably a flatbed color image scanning device or another suitable scanning device. The scanning device 102 (see FIG. 5) preferably has one or more off-axis inclined light sources 106 (see FIG. 5) housed within a housing 164 (see FIG. 6A) of the scanning device 102 (see FIG. 6A). The off-axis inclined light source 106 (see FIG. 5) may comprise a fluorescent light source, such as a fluorescent lamp or a cold cathode fluorescent lamp; a xenon light source, such as a xenon lamp; LED (light-emitting diode) lights, or another suitable light source. The off-axis inclined light source 106 (see FIG. 5) may be connected to a voltage regulator (not shown) to ensure consistency of light over the scan pass.

The scanning device 102 (see FIG. 5) may preferably have one off-axis inclined light source 106 (see FIG. 5). Alternatively, the scanning device 102 (see FIG. 5) may have more than one off-axis inclined light source 106 (see FIG. 5), such as two off-axis inclined light sources 106 (see FIG. 5). For example, for scanning of the composite laminate 28 (see FIG. 5) with the scanning device 102 (see FIG.

5) having two off-axis inclined light sources 106 (see FIG. 5), the off-axis inclined light sources 106 (see FIG. 5) may be controlled so that a first off-axis inclined light source is turned on and a second off-axis inclined light source is turned off during the first scan 104 (see FIG. 5). Then, with the second scan 126 (see FIG. 5), the first off-axis inclined light source is turned off and the second off-axis inclined light source is turned on.

In one embodiment, during the first scan 104, the off-axis inclined light source 106 may direct light 108, for example, at a +45° (plus forty-five degree) angle to the first area 112 (see FIG. 5) on the prepared edge 92a (see FIG. 5). The orientation 117 (see FIG. 5) of the off-axis inclined light source 106 (see FIG. 5) may then be rotated preferably in a 180 degree rotation 125a (see FIG. 5) relative to the prepared edge 92a (see FIG. 5) of the composite laminate 28 (see FIG. 5). Then, during the second scan 126 (see FIG. 5), the off-axis inclined light source 106 (see FIG. 5) may direct light 108 (see FIG. 5), for example, at a −45° (minus forty-five degree) angle to the first area 112 (see FIG. 5) on the prepared edge 92a (see FIG. 5).

Alternatively, during the first scan 104, the off-axis inclined light source 106 may direct light 108, for example, at a +45° (plus forty-five degree) angle to the first area 112 (see FIG. 5) on the prepared edge 92a (see FIG. 5). Then, the composite laminate 28 (see FIG. 5) may be physically rotated 180 degrees and scanned, such that during the second scan 126 (see FIG. 5), the off-axis inclined light source 106 (see FIG. 5) directs light 108 (see FIG. 5), for example, at a −45° (minus forty-five degree) angle to the first area 112 (see FIG. 5) on the prepared edge 92a (see FIG. 5). By rotating the composite laminate 28 (see FIG. 5) 180 degrees and then scanning, the orientation 117 (see FIG. 5) of the off-axis inclined light source 106 (see FIG. 5) is effectively also rotated 180 degrees relative to the prepared edge 92a (see FIG. 5) of the composite laminate 28 (see FIG. 5).

The step 70 (see FIG. 4A) of performing the first scan 104 (see FIG. 5) of the prepared edge 92a (see FIG. 5) and the step 74 (see FIG. 4A) of performing the second scan 126 (see FIG. 5) of the prepared edge 92a (see FIG. 5) preferably comprise using the scanning device 102 (see FIG. 5) having an optical resolution 122 (see FIG. 5) of 1200 dpi (dots per inch), or greater. The scanning device 102 (see FIG. 5) preferably has a hardware resolution of 1200×1200 dpi, or greater; a maximum resolution of 9600×9600 dpi, or greater; a scanning speed of 1.6 msec/line (milliseconds per line), or greater, for a black and white scan at 1200 dpi; and a scanning speed of 4.9 msec/line (milliseconds per line), or greater, for a color scan at 1200 dpi. However, the scanning device 102 (see FIG. 5) may have other suitable resolutions and speeds.

An example of a scanning device that may be used with the method 66 (see FIG. 4A), the method 80 (see FIG. 4B), and the system 90 (see FIG. 5) disclosed herein, includes, but is not limited to, an EPSON flatbed scanning device from Epson America, Inc. of Long Beach, Calif. (EPSON is a registered trademark of Seiko Epson Kabushiki Kaisha DBA Seiko Epson Corporation of Tokyo, Japan.) However, other suitable scanning devices may also be used.

As shown in FIG. 4A, the method 66 further comprises step 76 of comparing the first scanned image 116 (see FIG. 5) and the second scanned image 128 (see FIG. 5) to determine the ply orientation 98 (see FIG. 5) of each ply 94 (see FIG. 5) of the composite laminate 28 (see FIG. 5). The ply orientation 98 (see FIG. 5) is preferably determined based on light source reflections 124 (see FIG. 5) of the off-axis inclined light source 106 (see FIG. 5).

In one embodiment, the step 76 (see FIG. 4A) of comparing the first scanned image 116 (see FIG. 5) and the second scanned image 128 (see FIG. 5) to determine the ply orientation 98 (see FIG. 5) comprises a manual visual comparison 146a (see FIG. 5) of the light source reflections 124 (see FIG. 5) of the first scanned image 116 (see FIG. 5) and the second scanned image 128 (see FIG. 5). Preferably, the manual visual comparison 146a is performed by one or more operators of the method 66 (see FIG. 4A).

In another embodiment, the step 76 (see FIG. 4A) of comparing the first scanned image 116 (see FIG. 5) and the second scanned image 128 (see FIG. 5) to determine the ply orientation 98 (see FIG. 5) comprises using an automated comparison 146b (see FIG. 5) with a process software 154 (see FIG. 5) to compare the light source reflections 124 (see FIG. 5) of the first scanned image 116 (see FIG. 5) and the second scanned image 128 (see FIG. 5). In yet another embodiment, the step 76 (see FIG. 4A) of comparing the first scanned image 116 (see FIG. 5) and the second scanned image 128 (see FIG. 5) to determine the ply orientation 98 (see FIG. 5) may comprise using a combination of the manual visual comparison 146a (see FIG. 5) and the automated comparison 146b (see FIG. 5) with the process software 154 (see FIG. 5).

The step 76 (see FIG. 4A) of comparing the first scanned image (see FIG. 5) and the second scanned image 128 (see FIG. 5) to determine the ply orientation 98 (see FIG. 5) preferably comprises determining the ply orientation 98 (see FIG. 5) based on light source reflections 124 (see FIG. 5). Preferably, the light source reflections 124 (see FIG. 5) comprise bright/dark transition reflections 144a, 144b (see FIG. 5) in plies 142 (see FIG. 5) off-axis to the cross-section surface 114 (see FIG. 5) of the prepared edge 92a (see FIG. 5), such as +/−45° (plus/minus forty-five degree) plies 142a, 142b (see FIG. 5) to the cross-section surface 114 (see FIG. 5) of the prepared edge 92a (see FIG. 5). Preferably, the light source reflections 124 (see FIG. 5) further comprise dark reflections 136 (see FIG. 5) for plies 134 (see FIG. 5) normal or perpendicular to the cross-section surface 114 (see FIG. 5) of the prepared edge 92a (see FIG. 5), such as 90° (ninety degree) plies. Preferably, the light source reflections 124 (see FIG. 5) further comprise bright reflections 140 (see FIG. 5) for plies 138 (see FIG. 5) parallel to the cross-section surface 114 (see FIG. 5) of the prepared edge 92a (see FIG. 5), such as 0° (zero degree) plies.

As shown in FIG. 4A, the method 66 further comprises step 78 of verifying the ply orientation 98 (see FIG. 5) of the composite laminate 28 (see FIG. 5) against one or more baseline ply orientations 99 (see FIG. 5) of a baseline composite laminate 29 (see FIG. 5), and preferably against baseline ply orientations 99 (see FIG. 5) of a plurality of baseline plies 95 (see FIG. 5) of the baseline composite laminate 29 (see FIG. 5). The step 78 (see FIG. 4A) of verifying the ply orientation 98 (see FIG. 5) of the composite laminate 28 (see FIG. 5) comprises verifying that the plurality of plies 94 (see FIG. 5) of the composite laminate 28 (see FIG. 5) are laid up correctly as intended by design, such as a defined sequence of plies specified per design and/or quality requirements for the composite laminate 28 (see FIG. 5), for example, to optimize performance, such as load-carrying capacity.

Figure 8:
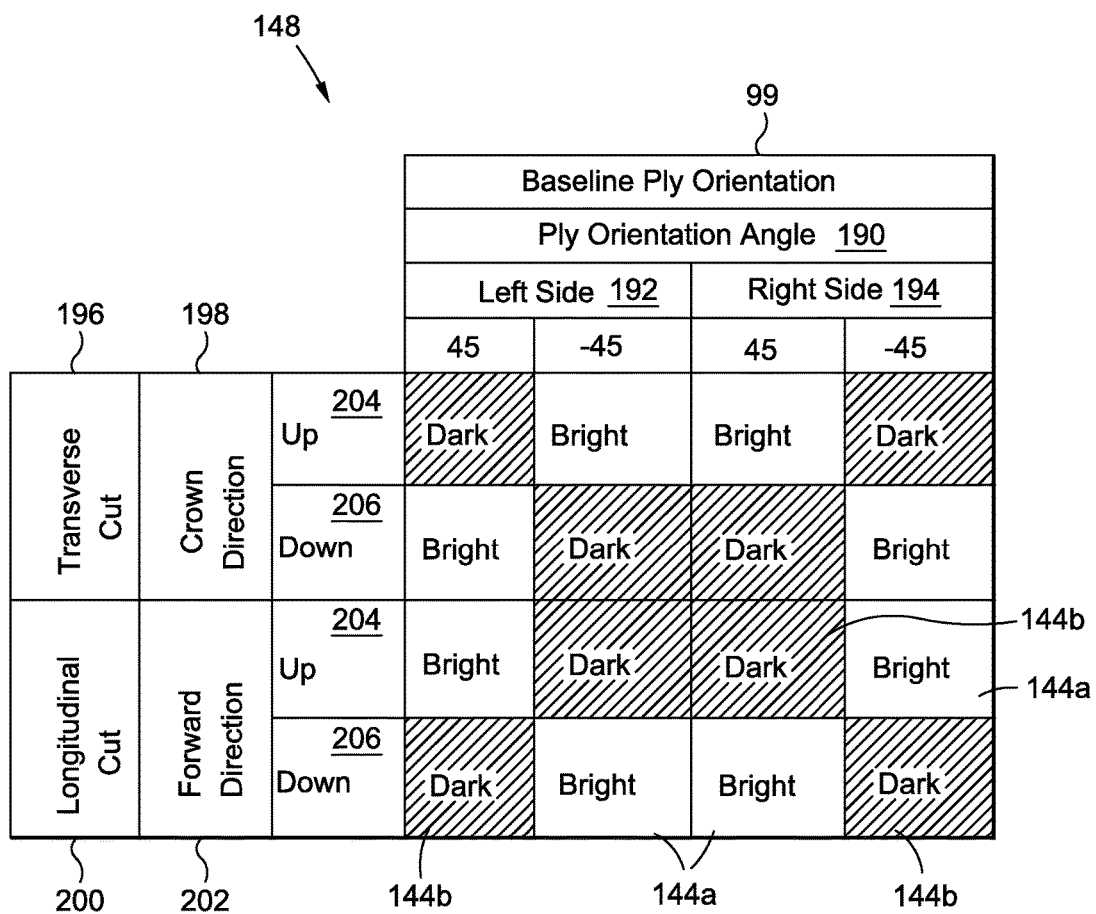

The method 66 (see FIG. 4A) may further optionally comprise prior to the verifying step 78 (see FIG. 4A), the step of preparing the baseline matrix 148 (see FIG. 5) comprising the baseline ply orientation 99 (see FIG. 5) of the plurality of baseline plies 95 (see FIG. 5) of the baseline composite laminate 29 (see FIG. 5). The baseline matrix 148, an example of which is shown in FIG. 8, may be prepared using a known composite laminate or known composite laminates with known ply orientations.

FIG. 4B shows the method 80 for determining and verifying ply orientation 98 (see FIG. 5) of the composite laminate 28 (see FIGS. 1, 5) of an aircraft composite structure 12 (see FIG. 1). As shown in FIG. 4B, the method 80 comprises step 82 of preparing the edge 92 (see FIG. 5) of the composite laminate 28 (see FIG. 5) to obtain the prepared edge 92a (see FIG. 5). One or more edges 92 (see FIG. 5) of the composite laminate 28 (see FIGS. 1, 5) may require one or more preparation treatments 93 (see FIG. 5) in order to obtain the prepared edge 92a that is smooth or polished prior to undergoing the method 80 (see FIG. 4B). As discussed above, preferably, the preparation treatments 93 (see FIG. 5) comprise one or more procedures, such as smoothing, polishing, abrading, finishing, cleaning, or another suitable preparation treatment for the edge 92a (see FIG. 5) of the composite laminate 28 (see FIG. 5). The preparation treatments 93 (see FIG. 5) may be performed manually or via automation, as discussed above. Preferably, the one or more preparation treatments 93 (see FIG. 5) of the edge 92 (see FIG. 5) facilitate visibility of the plurality of plies 94 (see FIG. 5) at the prepared edge 92a (see FIG. 5) in images of the prepared edge 92a, after the prepared edge 92a has been scanned.

As discussed above, the composite laminate 28 (see FIGS. 1, 5) is preferably in the form of a fiber-reinforced composite laminate 28a (see FIGS. 1, 5) comprised of a plurality of plies 94 (see FIG. 5). The plurality of plies 94 (see FIG. 5) preferably comprise continuous fibers 96 (see FIG. 5) in a resin matrix material 97 (see FIG. 5).

As shown in FIG. 4B, the method 80 further comprises step 83 of performing with the scanning device 102 (see FIG. 5) having at least one off-axis inclined light source 106 (see FIG. 5), a first scan 104 (see FIG. 5) of the prepared edge 92a (see FIG. 5) of the composite laminate 28 (see FIG. 5). The first scan 104 (see FIGS. 5, 6A) preferably uses the at least one off-axis inclined light source 106 (see FIG. 5) to direct light 108 (see FIG. 5) at the first acute angle 110 relative to the prepared edge 92a (see FIG. 5), to direct light 108 to the first area 112 (see FIG. 5) on the prepared edge 92a (see FIG. 5) to produce the first scanned image 116 (see FIG. 5).

As shown in FIG. 4B, the method 80 further comprises step 84 of rotating 180 degrees an orientation 117 (see FIG. 5) of the at least one off-axis inclined light source 106 (see FIG. 5) at a rotation 125 (see FIG. 5) relative to the prepared edge 92a (see FIG. 5) of the composite laminate 28 (see FIG. 5). As shown in FIG. 4B, the method 80 further comprises step 85 of performing with the scanning device 102 (see FIG. 5) a second scan 126 (see FIG. 5) of the prepared edge 92a (see FIG. 5) of the composite laminate 28 (see FIG. 5). With the orientation of the off-axis inclined light source rotated 180 degrees relative that of the first scan, the second scan 126 (see FIG. 5) uses the at least one off-axis inclined light source 106 (see FIG. 5) to direct light 108 (see FIG. 5) at the second acute angle 130 relative to the prepared edge 92a that is symmetrically opposite the first acute angle 110 (see FIG. 5), to direct light at a symmetrically opposite second acute angle 130 to the first area 112 (see FIG. 5) on the prepared edge 92a (see FIG. 5) to produce the second scanned image 128 (see FIG. 5).

As discussed above, in one embodiment, during the first scan 104, the off-axis inclined light source 106 (see FIG. 5) may direct light 108 (see FIG. 5), for example, at a +45° (plus forty-five degree) angle to the first area 112 (see FIG. 5) on the prepared edge 92a (see FIG. 5). The orientation 117 (see FIG. 5) of the off-axis inclined light source 106 (see FIG. 5) may then be rotated preferably in a 180 degree rotation 125a (see FIG. 5) relative to the prepared edge 92a (see FIG. 5) of the composite laminate 28 (see FIG. 5). Then, during the second scan 126 (see FIG. 5), the off-axis inclined light source 106 (see FIG. 5) rotated 180 degrees may direct light 108 (see FIG. 5), for example, at a −45° (minus forty-five degree) angle to the first area 112 (see FIG. 5) on the prepared edge 92a (see FIG. 5) that is symmetrically opposite to that employed in the first scan 104.

Alternatively, as discussed above, during the first scan 104 (see FIG. 5), the off-axis inclined light source 106 (see FIG. 5) may direct light 108 (see FIG. 5), for example, at a +45° (plus forty-five degree) angle to the first area 112 (see FIG. 5) on the prepared edge 92a (see FIG. 5). Then, the composite laminate 28 (see FIG. 5) is physically rotated preferably 180 degrees on the scanning device 102 (see FIG. 5) and scanned, such that during the second scan 126 (see FIG. 5), the off-axis inclined light source 106 (see FIG. 5) directs light 108 (see FIG. 5), for example, at a −45° (minus forty-five degree) angle to the first area 112 (see FIG. 5) on the prepared edge 92a (see FIG. 5).

The step 83 (see FIG. 4B) of performing the first scan 104 (see FIG. 5) of the prepared edge 92a (see FIG. 5) and the step 85 of performing the second scan 126 (see FIG. 5) of the prepared edge 92a (see FIG. 5) preferably comprise using the scanning device 102 (see FIG. 5) having a 45° (forty-five degree) light source 106a (see FIG. 5) and having an optical resolution 122 (see FIG. 5) of 1200 dpi (dots per inch), or greater. The specifics of the scanning device 102 (see FIG. 5) used in the method 66 (see FIG. 4A), as discussed above, apply equally to the scanning device 102 (see FIG. 5) used in the method 80 (see FIG. 4B).

As shown in FIG. 4B, the method 80 further comprises step 86 of transferring the first scanned image 116 (see FIG. 5) and the second scanned image 128 (see FIG. 5) from the scanning device 102 (see FIG. 5) to a processing device 150 (see FIG. 5) for processing. The first scanned image 116 (see FIG. 5) and the second scanned image 128 (see FIG. 5) may be converted into digital pixel information that may be transferred via one or more connection elements 152 (see FIG. 5) to the processing device 150 (see FIG. 5), such as in the form of a computer 150a (see FIG. 5), and saved as a digital file on the processing device 150 (see FIG. 5). The one or more connection elements 152 (see FIG. 5) may comprise wired cable connections or wireless connections. After the transfer, the digital file or files of the first scanned image 116 (see FIG. 5) and the second scanned image 128 (see FIG. 5) may, for example, be opened, saved, edited, deleted or printed.

As shown in FIG. 4B, the method 80 further comprises step 87 of comparing the first scanned image (see FIG. 5) and the second scanned image 128 (see FIG. 5) to determine the ply orientation 98 (see FIG. 5) of each ply 94 (see FIG. 5) of the composite laminate 28 (see FIG. 5). The ply orientation 98 (see FIG. 5) is preferably determined based on the light source reflections 124 (see FIG. 5) of the at least one off-axis inclined light source 106 (see FIG. 5).

The step 87 (see FIG. 4B) of comparing the first scanned image 116 (see FIG. 5) and the second scanned image 128 (see FIG. 5) to determine the ply orientation 98 (see FIG. 5) comprises using at least one of a manual visual comparison 146a (see FIG. 5) and/or an automated comparison 146b (see FIG. 5) with the process software 154 (see FIG. 5), to compare the light source reflections 124 (see FIG. 5) of the first scanned image 116 (see FIG. 5) and the second scanned image 128 (see FIG. 5). Preferably, the manual visual comparison 146a is performed by one or more operators of the method 80 (see FIG. 4B).

The step 87 (see FIG. 4B) of comparing the first scanned image (see FIG. 5) and the second scanned image 128 (see FIG. 5) to determine the ply orientation 98 (see FIG. 5) preferably comprises determining the ply orientation 98 (see FIG. 5) based on light source reflections 124 (see FIG. 5). Preferably, the light source reflections 124 (see FIG. 5) comprise bright/dark transition reflections 144a, 144b (see FIG. 5) in plies 142 (see FIG. 5) off-axis to the cross-section surface 114 (see FIG. 5) of the prepared edge 92a (see FIG. 5), such as +/−45° (plus/minus forty-five degree) plies 142a, 142b (see FIG. 5) to the cross-section surface 114 (see FIG. 5) of the prepared edge 92a (see FIG. 5). Preferably, the light source reflections 124 (see FIG. 5) further comprise dark reflections 136 (see FIG. 5) for plies 134 (see FIG. 5) normal or perpendicular to the cross-section surface 114 (see FIG. 5) of the prepared edge 92a (see FIG. 5), such as 90° (ninety degree) plies. Preferably, the light source reflections 124 (see FIG. 5) comprise bright reflections 140 (see FIG. 5) for plies 138 (see FIG. 5) parallel to the cross-section surface 114 (see FIG. 5) of the prepared edge 92a (see FIG. 5), such as 0° (zero degree) plies.

As shown in FIG. 4B, the method 80 further comprises step 88 of preparing the baseline matrix 148 (see FIG. 5) comprising the one or more baseline ply orientations 99 (see FIG. 5) of the baseline composite laminate 29 (see FIG. 5) of the aircraft composite structure 12 (see FIGS. 1, 5), and preferably, comprising the baseline ply orientations 99 (see FIG. 5) of a plurality of baseline plies 95 (see FIG. 5) of the baseline composite laminate 29 (see FIG. 5) of the aircraft composite structure 12 (see FIGS. 1, 5).

As shown in FIG. 4B, the method 80 further comprises step 89 of verifying the ply orientations 98 (see FIG. 5) of the composite laminate 28 (see FIG. 5) against the baseline ply orientation 99 (See FIG. 5) of the baseline matrix 148 (see FIG. 5), and in particular, against the baseline ply orientations 99 (see FIG. 5) of the plurality of baseline plies 95 (see FIG. 5) of the baseline composite laminate 29 (see FIG. 5). The step 89 (see FIG. 4B) of verifying the ply orientations 98 (see FIG. 5) of the composite laminate 28 (see FIG. 5) comprises verifying that the plurality of plies 94 (see FIG. 5) of the composite laminate 28 (see FIG. 5) are laid up correctly as intended by design, such as a defined sequence of plies specified per design and/or quality requirements for the composite laminate 28 (see FIG. 5), for example, to optimize performance, such as load-carrying capacity.

FIG. 5 shows the system 90 for determining and verifying ply orientation 98 of the composite laminate 28. The system 90 (see FIG. 5) comprises the composite laminate 28 (see FIG. 5) that is cured. As shown in FIG. 5, the composite laminate 28, comprises at least one prepared edge 92a and the plurality of plies 94. Each ply 94 (see FIG. 5) has a ply orientation 98 (see FIG. 5). The composite laminate 28 (see FIG. 5) is preferably a fiber-reinforced composite laminate 28a (see FIG. 5) comprised of continuous fibers 96 (see FIG. 5) in a resin matrix material 97 (see FIG. 5).

As discussed above, the composite laminate 28 (see FIG. 5) may have one or more edges 92 (see FIG. 5) that may require one or more preparation treatments 93 (see FIG. 5) in order to obtain the prepared edge 92a (see FIG. 5) that is smooth or polished prior to being scanned and analyzed. Preferably, the preparation treatments 93 (see FIG. 5) comprise one or more procedures such as smoothing, polishing, abrading, finishing, cleaning or another suitable preparation treatment for the edge 92a (see FIG. 5) of the composite laminate 28 (see FIG. 5). The preparation treatments 93 (see FIG. 5) may be performed manually or via automation, as discussed above. Preferably, the prepared edge 92a (see FIG. 5) facilitates visibility of the plurality of plies 94 (see FIG. 5) at the prepared edge 92a (see FIG. 5) after the prepared edge 92a is scanned.

As shown in FIG. 5, the system 90 further comprises a scanning assembly 100. The scanning assembly 100 (see FIG. 5) comprises the scanning device 102 (see FIG. 5) having at least one off-axis inclined light source 106 (see FIG. 5). Preferably, the at least one off-axis inclined light source 106 (see FIG. 5) comprises at least one 45° (forty-five degree) light source 106a (see FIG. 5). The scanning device 102 (see FIG. 5) is preferably a flatbed color scanning device, as discussed above, and preferably has an optical resolution 122 (see FIG. 5) of 1200 dpi (dots per inch), or greater.

The at least one off-axis inclined light source 106 (see FIG. 5) is preferably configured to direct light 108 (see FIG. 5) at the first angle 110 (see FIG. 5) to the first area 112 (see FIG. 5) on the prepared edge 92a (see FIG. 5) of the composite laminate 28 (see FIG. 5) to illuminate and capture the first scanned image 116 (see FIG. 5). As shown in FIG. 5, the first scan 104 produces the first scanned image 116, such as in the form of a first cross-sectional scanned image 116a.

The off-axis inclined light source 106 (see FIG. 5) of the scanning device 102 (see FIG. 5) is further configured to direct light 108 (see FIG. 5) at the second angle 130 (see FIG. 5) to the first area 112 (see FIG. 5) on the prepared edge 92a (see FIG. 5) to illuminate and capture the second scanned image 128 (see FIG. 5). As shown in FIG. 5, the second scan 126 produces the second scanned image 128, such as in the form of a second cross-sectional scanned image 128a.

The scanning device 102 (see FIG. 5) performs the first scan 104 and the second scan 126 in a scan direction 120 (see FIG. 5). During the first scan 104 (see FIG. 5), the off-axis inclined light source 106 (see FIG. 5) moves along a light source travel path 118 (see FIG. 5) to illuminate and capture the first scanned image 116 (see FIG. 5). During the second scan 126 (see FIG. 5), the off-axis inclined light source 106 (see FIG. 5) moves along the light source travel path 118 (see FIG. 5) to illuminate and capture the second scanned image 128 (see FIG. 5). As shown in FIG. 5, between the first scan 104 and the second scan 126, the orientation 117 of the at least one off-axis inclined light source 106 is rotated at a rotation 125, preferably a 180 degree rotation 125a, relative to the prepared edge 92a of the composite laminate 28.

As shown in FIG. 5, the scanning assembly 100 further comprises the processing device 150 coupled to the scanning device 102 (see FIG. 5). The processing device 150 (see FIG. 5) is preferably configured to receive and process the first scanned image 116 (see FIG. 5) and the second scanned image 128 (see FIG. 5) via one or more connection elements 152 (see FIG. 5) from the scanning device 102 (see FIG. 5). As shown in FIG. 5, the processing device 150 is preferably in the form of a computer 150a. As further shown in FIG. 5, the processing software 154, storage media 156, and a printing mechanism 158 may also be used with the processing device 150 to process, store, and print the first scanned image 116 and the second scanned image 128.

The processing device 150 (see FIG. 5) may comprise any of a wide variety of computers 150a (see FIG. 5) now known in the art or that may be developed in the future. By way of example only, the computer 150a may consist of a personal computer, including a desktop computer, a laptop computer, a notebook computer, or another suitable computer.

The processing device 150 (see FIG. 5) may preferably additionally include various other components and features known in the art, such as a central processing unit (CPU), system memory, an operating system, a plurality of applications, one or more input/output interfaces(s) that interface with corresponding input/output device(s), one or more communications interface(s) that may interface with other computer system(s) or computer networks, or other suitable components.

The storage media 156 (see FIG. 5) may comprise computer readable storage media for storing such items as process data, an algorithm, a computer readable software program (code), or other suitable items. The storage media 156 may comprise any suitable computer readable storage media, such as read only memory (ROM), random access memory (RAM), video memory (VRAM), hard disk, floppy diskette, compact disc (CD), magnetic tape, a combination thereof, or another suitable computer readable storage device.

The printing mechanism 158 (see FIG. 5) preferably comprises a printer or other suitable output device for displaying or outputting the first scanned image 116 and the second scanned image 128, whether textually or graphically. In other embodiments, any number of suitable peripheral devices (e.g., monitor, printer, keyboard, mouse, or other devices) may be connected to the processing device 150, either directly or indirectly.

The process software 154 (see FIG. 5) may implement an algorithm designed to be used in conjunction with the processing device 150 (see FIG. 5), such as the computer 150a (hardware). The algorithm of the process software 154 (see FIG. 5) may facilitate processing of the first scanned image 116 and the second scanned image 128. As used herein, "algorithm" means a set of instructions or list of steps for performing a task or solving a problem.

FIG. 5 further shows the scanning assembly 100 comprising one or more controllers 160 for controlling the scanning device 102 and/or the processing device 150. The controllers 160 may comprise motor controllers, electrical controllers, software control systems, or other suitable controller devices or mechanisms. FIG. 5 further shows the scanning assembly 100 comprising one or more power sources 162 for providing power to the scanning device 102 and/or the processing device 150. The power sources 162 may comprise motors, batteries, electrical power systems, or other suitable power sources.

FIG. 5 further shows the scanning assembly 100 comprising the baseline matrix 148 (see also FIG. 8) comprising the baseline ply orientation(s) 99 of the plurality of baseline plies 95 of the baseline composite laminate 29. The processing device 150 (see FIG. 5) preferably processes the first scanned image 116 (see FIG. 5) and the second scanned image 128 (see FIG. 5) to enable comparison of the first scanned image 116 (see FIG. 5) and the second scanned image 128 (see FIG. 5) against each other and against the baseline matrix 148 (see FIG. 5).

As shown in FIG. 5, the system 90 provides a ply orientation determination 146 of each ply 94 of the composite laminate 28 based on light source reflections 124 of the at least one off-axis inclined light source 106 and a comparison of the first scanned image 116 and the second scanned image 126. The ply orientation determination 146 (see FIG. 5) may be determined using a manual visual comparison 146a (see FIG. 5) and/or an automated comparison 146b (see FIG. 5) with the process software 154 (see FIG. 5), to compare the light source reflections 124 (see FIG. 5) of the first scanned image 116 (see FIG. 5) and the second scanned image 128 (see FIG. 5). Preferably, the manual visual comparison 146a is performed by one or more operators of the system 90 (see FIG. 5).

The ply orientation determination 146 (see FIG. 5) is preferably based on light source reflections 124 (see FIG. 5). Preferably, the light source reflections 124 (see FIG. 5) comprise bright/dark transition reflections 144a, 144b (see FIG. 5) in plies 142 (see FIG. 5) off-axis to the cross-section surface 114 (see FIG. 5) of the prepared edge 92a (see FIG. 5), such as +/−45° (plus/minus forty-five degree) plies 142a, 142b. Preferably, the light source reflections 124 (see FIG. 5) further comprise dark reflections 136 (see FIG. 5) for plies 134 (see FIG. 5) normal or perpendicular to the cross-section surface 114 (see FIG. 5) of the prepared edge 92a (see FIG. 5), such as 90° (ninety degree) plies. Preferably, the light source reflections 124 (see FIG. 5) further comprise bright reflections 140 (see FIG. 5) for plies 138 (see FIG. 5) parallel to the cross-section surface 114 (see FIG. 5) of the prepared edge 92a (see FIG. 5), such as 0° (zero degree) plies.

The ply orientation 98 (see FIG. 5) may cause a differential scanning brightness 132 (see FIG. 5) of the plurality of plies 94 (see FIG. 5) at the prepared edge 92a (see FIG. 5) when the prepared edge 92a (see FIG. 5) of the composite laminate 28 (see FIG. 5) is scanned. The differential scanning brightness 132 (see FIG. 5) of the plurality of plies 94 may result in scanned images showing dark plies, bright plies, brightest plies, or another variation of brightness or darkness of the plies. The differential scanning brightness 132 (see FIG. 5) may be used to verify ply orientation 98 (see FIG. 5). As shown in FIG. 5, the system 90 further provides a ply orientation verification 147 of the composite laminate 28 using the baseline matrix 148.

Figure 6A:
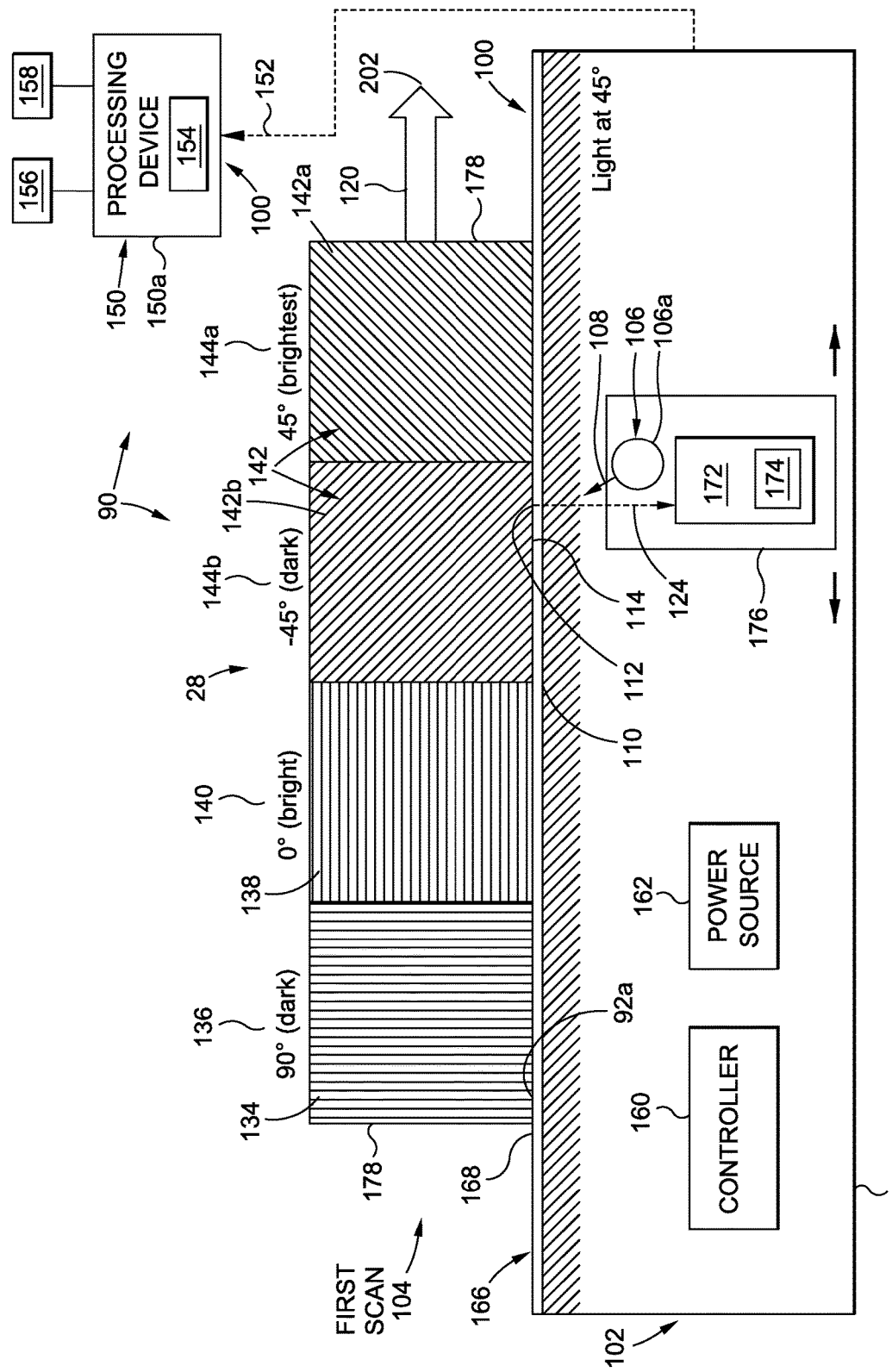
FIG. 6A is a schematic illustration of a side view of an embodiment of a system for determining and verifying ply orientation of a composite laminate, where the composite laminate is undergoing a first scan.

FIG. 6A is a schematic illustration of a side view of an embodiment of the system 90 for determining and verifying ply orientation 98 (see FIG. 5) of the composite laminate 28, where the composite laminate 28 is undergoing a first scan 104. As shown in FIG. 6A, the system 90 comprises the composite laminate 28 having a prepared edge 92a that is to be scanned and analyzed with the scanning assembly 100. The composite laminate 28 (see FIG. 6A) is preferably in the form of a sample portion or coupon. As shown in FIG. 6A, the composite laminate 28 is positioned on the scanning device 102 of the scanning assembly 100. The scanning device 102 (see FIG. 6A) is preferably a flatbed color scanning device or other suitable scanning device, as discussed above. The processing device 150 (see FIG. 6A) is connected to the scanning device 102 (see FIG. 6A) via connection element 152 (see FIG. 6A).

As further shown in FIG. 6A, the scanning device 102 includes a housing 164 that houses the controller 160, the power source 162, such as in the form of a motor, and a movable carrier 176. The off-axis inclined light source 106 (see FIG. 6A), such as in the form of a 45° (forty-five degree) light source 106a (see FIG. 6A), is shown mounted on the movable carrier 176, along with an image capture assembly 172. The movable carrier 176 (see FIG. 6A) preferably moves up and down the length of the scanning device 102 at a constant rate and is preferably driven by the motor.

The image capture assembly 172 (see FIG. 6A) may include one or more image sensors 174 (see FIG. 6A) and/or other various components (not shown), such as an optical assembly of reflective mirrors and a lens unit, as known in the art. The one or more image sensors 174 (see FIG. 6A) may comprise a charge coupled device (CCD) array, a complementary metal-oxide semiconductor (CMOS) type image sensor, a contact image sensor (CIS), or another suitable image sensor. The one or more image sensors 174 (see FIG. 6A) preferably contain light-sensitive diodes that convert analog light waves into digital signals and that enable conversion of the light source reflections 124 (see FIG. 6A) into digital pixel information that is transferred as the first scanned image 116 (see FIG. 5) and the second scanned image 128 (see FIG. 5) to the processing device 150 (see FIGS. 6A, 6B).

The scanning device 102 (see FIG. 6A) further comprises a glass plate 166 (see FIG. 6A). As shown in FIG. 6A, the prepared edge 92*a* of the composite laminate 28, in the form of a sample to be analyzed and scanned, is placed on a top surface 168 of the glass plate 166. A lid (not shown) of the scanning device 102 (see FIG. 6A) may be closed over the composite laminate 28 or may be left open during scanning of the composite laminate 28. FIG. 6A shows the composite laminate 28 with sides 178 and positioned in at a forward direction 202 in the scan direction 120. The sides 178 (see FIG. 6A) of the fibers in the plurality of plies 94 (see FIG. 5) reflect more light than the fiber ends.

As shown in FIG. 6A, during the first scan 104, the off-axis inclined light source 106 directs light 108 at a first angle 110, such as in the form of a 45° (forty-five degree) angle, to the first area 112 on the prepared edge 92*a*. The light 108 (see FIG. 6A) illuminating the first area 112 (see FIG. 6A) reflects back as a light source reflection 124 (see FIG. 6A). The image sensors 174 (see FIG. 6A) sense the light source reflection 124 (see FIG. 6A) and convert the light source reflection 124 (see FIG. 6A) into digital pixel information that is transferred as the first scanned image 116 (see FIG. 5) to the processing device 150 (see FIG. 6A), such as in the form of computer 150*a* (see FIG. 6A). The first scanned image 116 (see FIG. 5) is preferably processed with process software 154 (see FIG. 6A) and may be stored in storage media 156 (see FIG. 6A) and/or printed with a printing mechanism 158 (see FIG. 6A).

As shown in FIG. 6A, the composite laminate 28 includes plies 134, such as 90° (ninety degree) plies, normal or perpendicular to the cross-section surface 114 of the prepared edge 92*a*, and also normal or perpendicular to the surface 168 of the glass plate 166. As further shown in FIG. 6A, the plies 134, such as 90° (ninety degree) plies, exhibited dark reflections 136 when scanned in the first scan 104.

As shown in FIG. 6A, the composite laminate 28 further includes plies 138, such as 0° (zero degree) plies, parallel to the cross-section surface 114 of the prepared edge 92*a*, and also parallel to the surface 168 of the glass plate 166. As further shown in FIG. 6A, the plies 138, such as 0° (zero degree) plies, exhibited bright reflections 140 when scanned in the first scan 104.

As shown in FIG. 6A, the composite laminate 28 further includes plies 142, such as −45° (minus forty-five degree) plies 142*b* and 45° (forty-five degree) plies 142*a*, off-axis to the cross-section surface 114 of the prepared edge 92*a*, and also off-axis to the surface 168 of the glass plate 166. As further shown in FIG. 6A, the plies 142*b*, such as −45° (minus forty-five degree) plies, exhibited dark transition reflections 144*b* when scanned in the first scan 104. As further shown in FIG. 6A, the plies 142*a*, such as 45° (forty-five degree) plies, exhibited brightest transition reflections 144*a* when scanned in the first scan 104.

Figure 6B:
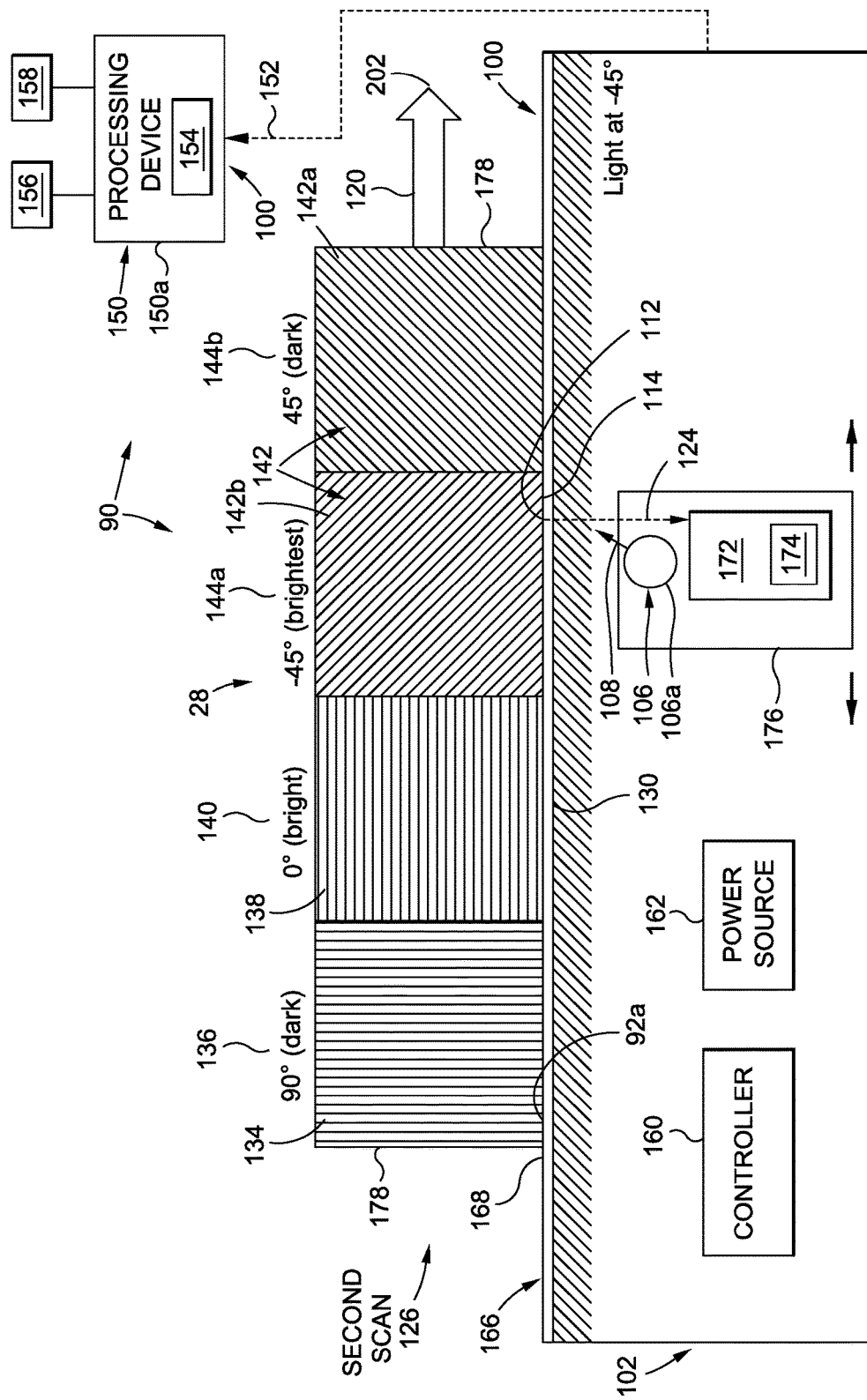
FIG. 6B is a schematic illustration of a side view of the system for determining and verifying ply orientation of the composite laminate of FIG. 6A, where the composite laminate is undergoing a second scan.

FIG. 6B is a schematic illustration of a side view of the system 90 for determining and verifying ply orientation 98 (see FIG. 5) of the composite laminate 28 of FIG. 6A, where the composite laminate 28 is undergoing a second scan 126. As shown in FIG. 6B, the system 90 includes the composite laminate 28 positioned on the scanning device 102 of the scanning assembly 100 of FIG. 6A, and the processing device 150 connected to the scanning device 102 via connection element 152. The components of the system 90 in FIG. 6B are identical to FIG. 6A except that the orientation 117 (see FIG. 5) of the off-axis inclined light source 106 (see FIG. 6B) is now rotated in a 180 degree rotation 125*a* (see FIG. 5) relative to the prepared edge 92*a* (see FIG. 6B) of the composite laminate 28 (see FIG. 6B). Prior to performing the second scan 126, the orientation 117 (see FIG. 5) of the off-axis inclined light source 106 (see FIG. 5) is rotated at a rotation 125 (see FIG. 5), such as a 180 degree rotation 125*a* (see FIG. 5), relative to the prepared edge 92*a* (see FIG. 6B) of the composite laminate 28 (see FIG. 6B).

As shown in FIG. 6B, during the second scan 126, the off-axis inclined light source 106, such as the 45° (forty-five degree) light source 106*a*, directs light 108 at a second angle 130, such as in the form of a −45° (minus forty-five degree) angle, to the first area 112 on the prepared edge 92*a*. The light 108 (see FIG. 6B) illuminating the first area 112 (see FIG. 6B) reflects back as the light source reflection 124 (see FIG. 6B). The image sensors 174 (see FIG. 6B) sense the light source reflection 124 (see FIG. 6B) and convert the light source reflection 124 (see FIG. 6B) into digital pixel information that is transferred as the second scanned image 128 (see FIG. 5) to the processing device 150 (see FIG. 6B), such as in the form of computer 150*a* (see FIG. 6B). The second scanned image 128 (see FIG. 5) is preferably processed with the process software 154 (see FIG. 6B) and may be stored in storage media 156 (see FIG. 6B) and/or printed with the printing mechanism 158 (see FIG. 6B).

As shown in FIG. 6B, the composite laminate 28 includes plies 134, such as 90° (ninety degree) plies, normal or perpendicular to the cross-section surface 114 of the prepared edge 92*a*, and normal or perpendicular to the surface 168 of the glass plate 166. As further shown in FIG. 6B, the plies 134, such as 90° (ninety degree) plies, exhibited dark reflections 136 when scanned with the second scan 126.

As shown in FIG. 6B, the composite laminate 28 further includes plies 138, such as 0° (zero degree) plies, parallel to the cross-section surface 114 of the prepared edge 92*a*, and parallel to the surface 168 of the glass plate 166. As further shown in FIG. 6B, the plies 138, such as 0° (zero degree) plies, exhibited bright reflections 140 when scanned with the second scan 126.

As shown in FIG. 6B, the composite laminate 28 further includes plies 142, such as −45° (minus forty-five degree) plies 142*b* and 45° (forty-five degree) plies 142*a*, off-axis to the cross-section surface 114 of the prepared edge 92*a*, and off-axis to the surface 168 of the glass plate 166. As further shown in FIG. 6B, the plies 142*b*, such as −45° (minus forty-five degree) plies, exhibited brightest transition reflections 144*a* when scanned with the second scan 126. As further shown in FIG. 6B, the plies 142*a*, such as 45° (forty-five degree) plies, exhibited dark transition reflections 144*b* when scanned with the second scan 126.

In an analysis of the first scanned images 116 (see FIG. 5) from the first scan 104 as shown in FIG. 6A, and in an analysis of the second scanned images 128 (see FIG. 5) from the second scan 126 as shown in FIG. 6B, it was found that in both the first scan 104 and the second scan 126, that both 0° (zero degree) plies and 90° (ninety degree) plies perpendicular to the surface 168 (see FIG. 6A) of the glass plate 166 (see FIG. 6A) always appeared dark and exhibited dark reflections 136 when scanned. It was further found that in both the first scan 104 and the second scan 126, that both 0° (zero degree) plies and 90° (ninety degree) plies parallel to the surface 168 (see FIG. 6A) of the glass plate 166 (see FIG. 6A) always appeared bright with streaks and exhibited bright reflections 140 when scanned.

It was further found that in both the first scan 104 and the second scan 126, that the brightness of the +/−45° (plus/minus forty-five degree) plies depended on whether the ply was oriented parallel or perpendicular to the light 108 (see FIGS. 6A-6B) from the off-axis inclined light source 106 (see FIGS. 6A-6B). Which plies exhibited bright or dark reflections depended on whether the composite laminate 28 sample was cut at a transverse cut 196 (see FIG. 8) or a longitudinal cut 200 (see FIG. 8), depended on which side of the aircraft 10 (see FIG. 1) the composite laminate 28 sample was obtained from, such as the left side 192 (see FIG. 8) or the right side 194 (see FIG. 8), and depended on the orientation of the composite laminate 28 sample, such as orientation in a crown direction 198 (see FIG. 8) or orientation in a forward direction 202 (see FIGS. 6A-6B, 8).

Figure 7:
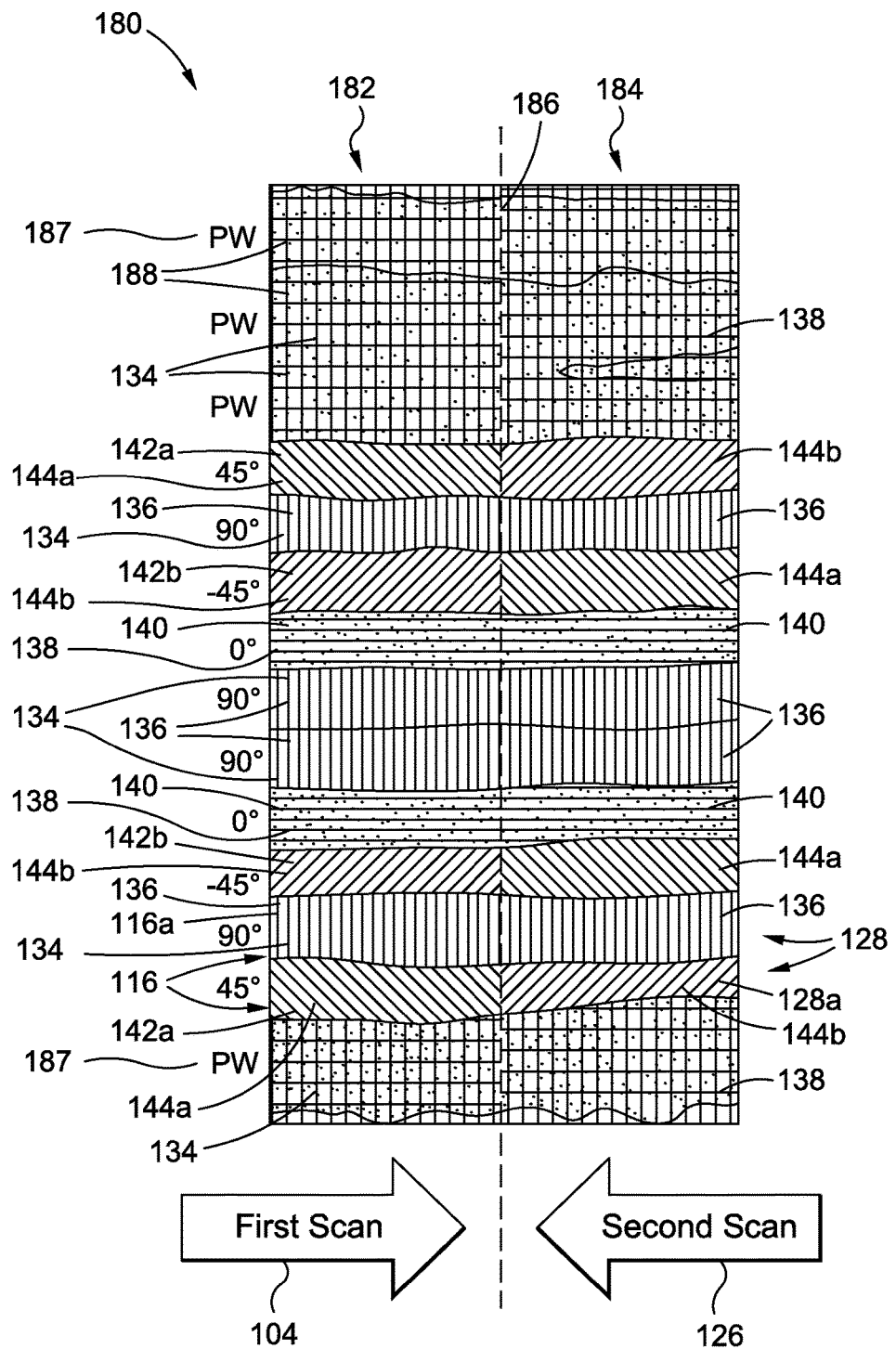
FIG. 7 is a schematic illustration of side-by-side scanned images of first scanned images taken by first scans and second scanned images taken by second scans of a prepared edge of a composite laminate obtained using one of the embodiments of a method and a system of the disclosure; and, FIG. 8 is an illustration of an embodiment of a baseline matrix that may be used in one of the embodiments of a method and a system for determining and verifying ply orientation of the composite laminate of the disclosure.

FIG. 7 is a schematic illustration of side-by-side scanned images 180 of first scanned images 116, such as in the form of first cross-sectional scanned images 116a, taken by first scans 104, and second scanned images 128, such as in the form of second cross-sectional scanned images 128a, taken by second scans 126. Both the first scans 104 and the second scans 126 were taken of the prepared edge 92a (see FIGS. 6A-6B) of the composite laminate 28 (see FIGS. 6A-6B) obtained using one of the embodiments of the method 66 (see FIG. 4A), the method 80 (see FIG. 4B), and the system 90 (see FIG. 5) for determining and verifying ply orientation 98 (see FIG. 5) of the composite laminate 28 (see FIG. 5). As shown in FIG. 7, the side-by-side scanned images 180 comprise a first half 182 consisting of the first scanned images 116, and a second half 184 consisting of the second scanned images 128. As further shown in FIG. 7, the first scanned images 116 and the second scanned images 128 are divided by a dotted line 186.

In obtaining the first scanned images 116 and the second scanned images 128 shown in FIG. 7, sample coupons of the composite laminate 28 (see FIG. 5) were cut with a mill saw at a longitudinal cut 200 (see FIG. 8) at a 0° (zero degree) ply orientation angle 190 (see FIG. 5). An edge 92 (see FIG. 5) of the cut composite laminate 28 (see FIG. 5) was prepared by a preparation treatment 93 (see FIG. 5) consisting of polishing the edge 92 for about 10 (ten) minutes. A first scan 104 and a second scan 126 for each ply orientation shown in FIG. 7, i.e., 0°, 90°, 45°, −45° and PW, were taken, with the scanning device 102 (see FIGS. 6A-6B), and each scan was performed in about 5 (five) minutes. The first scans 104 and the second scans 126 were taken with cross-section surfaces 114 (see FIG. 5) of the composite laminate 28 samples parallel to the scan direction 120 (see FIGS. 5, 6A).

As shown in FIG. 7, the first scanned images 116 and the second scanned images 128 included scanned images of plies 138, such as 0° (zero degree) plies, parallel to the cross-section surface 114 (see FIGS. 6A-6B) of the prepared edge 92a (see FIG. 5). As further shown in FIG. 7, both the first scan 104 of the 0° (zero degree) plies and the second scan 126 of the 0° (zero degree) plies exhibited bright reflections 140.

As further shown in FIG. 7, the first scanned images 116 and the second scanned images 128 included scanned images of plies 134, such as 90° (ninety degree) plies, normal to the cross-section surface 114 (see FIGS. 6A-6B) of the prepared edge 92a (see FIG. 5). As further shown in FIG. 7, both the first scan 104 of the 90° (ninety degree) plies and the second scan 126 of the 90° (ninety degree) plies exhibited dark reflections 140.

As further shown in FIG. 7, the first scanned images 116 and the second scanned images 128 included scanned images of 45° (forty-five degree) plies 142a off-axis to the cross-section surface 114 (see FIGS. 6A-6B) of the prepared edge 92a (see FIG. 5). As further shown in FIG. 7, the first scan 104 of the 45° (forty-five degree) plies 142a exhibited brightest reflections 144a, and the second scan 126 of the 45° (forty-five degree) plies exhibited dark reflections 144b.

As further shown in FIG. 7, the first scanned images 116 and the second scanned images 128 included scanned images of −45° (minus forty-five degree) plies 142b off-axis to the cross-section surface 114 (see FIGS. 6A-6B) of the prepared edge 92a (see FIG. 5). As further shown in FIG. 7, the first scan 104 of the −45° (minus forty-five degree) plies 142b exhibited dark reflections 144b, and the second scan 126 of the −45° (minus forty-five degree) plies exhibited brightest reflections 144a.

FIG. 7 shows the first scanned images 116 and the second scanned images 128 included PW plies 187. PW plies 187 comprise a type of woven fabric consisting of a mixture of plies 134, such as 90° (ninety degree) plies, normal to the cross-section surface 114 (see FIGS. 6A-6B) of the prepared edge 92a (see FIG. 5), and plies 138, such as 0° (zero degree) plies, parallel to the cross-section surface 114 (see FIGS. 6A-6B) of the prepared edge 92a (see FIG. 5). As shown in FIG. 7, both the first scan 104 of the PW plies 187 and the second scan 126 of the PW plies 187 exhibited speckled dark/bright mixture reflections 188.

FIG. 8 is an illustration of an embodiment of the baseline matrix 148 that was used as the ply orientation verification 147 (see FIG. 5) for the ply orientations 98 (see FIG. 5) of the plurality of plies 94 (see FIG. 5) shown in FIG. 7. The baseline matrix 148, as shown in FIG. 8, was created by using a known composite laminate or known composite laminates, such as composite skins, with known ply orientations, to verify the ply orientation 98 (see FIG. 5) determined from the first scans 104 and second scans 126 shown in FIG. 7. The baseline matrix 148 shown in FIG. 8 is merely an example of one baseline matrix 148 that may be used with one of the embodiments of the method 66 (see FIG. 4A), the method 80 (see FIG. 4B), and the system 90 (see FIG. 5) for determining and verifying ply orientation 98 (see FIG. 5) of the composite laminate 28 (see FIG. 5). The baseline matrix 148 (see FIG. 8) may be modified depending on the baseline ply orientation 99 (see FIG. 8) and ply orientation angles 190 (see FIG. 8) of the plurality of baseline plies 95 (see FIG. 5) that make up the baseline composite laminate 29 (see FIG. 8) used as a baseline to verify a composite laminate 28 (see FIG. 5).

As shown in FIG. 8, the baseline matrix 148 shows the baseline ply orientation 99 having the ply orientation angles 190 of 45° (forty-five degrees) and −45° (minus forty-five degrees). As further shown in FIG. 8, the baseline matrix 148 shows the baseline composite laminate 29 (see FIG. 5) samples were obtained from the left side 192 and the right side 194 of the aircraft 10 (see FIG. 1). As further shown in FIG. 8, the baseline matrix 148 shows the baseline composite laminate 29 samples were cut at a transverse cut 196 and a longitudinal cut 200 and were oriented in a crown direction 198, either up 204 of down 206, and were oriented in a forward direction 202, either up 204 of down 206.

As shown in FIG. 8, the light source reflections 124 (see FIG. 5) of the 45° (forty-five degree) plies exhibited both dark transition reflections 144b and bright transition reflections 144a on the left side 192 and the right side 194. As further shown in FIG. 8, the light source reflections 124 (see FIG. 5) of the −45° (minus forty-five degree) plies exhibited both bright transition reflections 144a and dark transition reflections 144b on the left side 192 and on the right side 194. The baseline matrix 148 shows the differential scanning brightness 132 (see FIG. 5) of the each of the +/−45° (plus/minus forty-five degree) plies with the bright/dark transition reflections 144a, 144b. The differential scanning brightness 132 may also be used to verify the ply orientation 98 (see FIG. 5)

Disclosed embodiments of the method 66 (see FIG. 4A), the method 80 (see FIG. 4B), and the system 90 (see FIG. 5) provide numerous advantages over known methods and systems, including providing a quick process for determining and verifying the ply orientation 98 (see FIG. 5) of composite laminates 28 (see FIG. 5) that are cured, so as to maintain uniformity and consistency of the composite laminates 28 (see FIG. 5) and to comply with design and/or quality requirements for the composite laminates 28 (see FIG. 5). In addition, disclosed embodiments of the method 66 (see FIG. 4A), the method 80 (see FIG. 4B), and the system 90 (see FIG. 5) provide a process and system that may substantially reduce the time, labor, equipment, and costs for determining and verifying ply orientation of composite laminates 28 (see FIG. 5), as compared to known methods and systems for determining and verifying ply orientation. Known methods and systems may be very time consuming and may take several days to complete, may be labor intensive and tedious, and may require increased equipment, all which may, in turn, result in increased manufacturing time and expense.

Moreover, disclosed embodiments of the method 66 (see FIG. 4A), the method 80 (see FIG. 4B), and the system 90 (see FIG. 5) involve performing a first scan 104 and a second scan 126 of just the prepared edge 92a the composite material 28 (see FIG. 5) to determine the ply orientation 98 (see FIG. 5) of the plurality of plies 94 (see FIG. 5) which make up the composite laminate 28 (see FIG. 5), The prepared edge 92a (see FIG. 5) is preferably scanned from two different angles, including a first angle 110 (see FIGS. 5, 6A) and a second angle 130 (see FIGS. 5, 6B). Unlike known methods and systems for determining and verifying ply orientation, disclosed embodiments of the method 66 (see FIG. 4A), the method 80 (see FIG. 4B), and the system 90 (see FIG. 5) do not require extensive polishing of the edge 92 (see FIG. 5) of the composite laminate 28 (see FIG. 5) prior to scanning, do not require mounting of the composite laminate 28 (see FIG. 5) in order to be polished, do not require a plurality of microscopic images be taken and edited together to enable sufficient visibility under a microscope, and do not require labor intensive analysis of each ply to discern the difference between 0° (zero degree) plies and +/−45° (plus/minus forty-five degree) plies. Further, unlike known methods and systems for determining and verifying ply orientation, disclosed embodiments of the method 66 (see FIG. 4A), the method 80 (see FIG. 4B), and the system 90 (see FIG. 5) do not require a second cut be made of the composite laminate 28 (see FIG. 5) sample coupon, and do not require a repeat process and analysis of the second cut to sufficiently distinguish between +/−45° (plus/minus forty-five degree) plies to comply with qualification requirements.

In addition, disclosed embodiments of the method 66 (see FIG. 4A), the method 80 (see FIG. 4B), and the system 90 (see FIG. 5) utilize a 45° (forty-five degree) light source 106a (see FIG. 5) from a scanning device 102 (see FIG. 5) and images the composite laminate 28 (see FIG. 5) oriented transverse to the light source travel path 118 (see FIG. 5) twice, with a 180 degree rotation 125a (see FIG. 5) between scanning of the first scanned image 116 and scanning of the second scanned image 128. The first scanned image 116 (see FIG. 5) and the second scanned image 128 (see FIG. 5) preferably provide opposite bright/dark transition reflections 144a, 144b (see FIG. 5) in plies +/−45° (plus/minus forty-five degrees) from the cross-section surface 114 (see FIG. 5) of the prepared edge 92a (see FIG. 5), while maintaining dark reflections 136 for plies 134 (see FIG. 5) normal to the cross-section surface 114 (see FIG. 5) of the prepared edge 92a (see FIG. 5), and bright reflections 140 (see FIG. 5) for plies 138 (see FIG. 5) parallel to the cross-section surface 114 (see FIG. 5) of the prepared edge 92a (see FIG. 5). Using the process software 154 (see FIG. 5), a complete ply orientation 98 (see FIG. 5) of the composite laminate 28 (see FIG. 5) may be determined.

Further, disclosed embodiments of the method 66 (see FIG. 4A), the method 80 (see FIG. 4B) and the system 90 (see FIG. 5) provide an efficient process where the number of polishing and preparing steps for preparing an edge 92 (see FIG. 5) prior to scanning may be reduced and a lower polish finish may be obtained from a typical 240 grit sandpaper with a 0.05 μm (micron) finish to a 600 grit sandpaper with a 0.06 μm (micron) finish, as the shape of the fiber at the cross-section is no longer being interrogated. Rather, the light source reflections 124 (see FIG. 5) from two opposite angled off-axis inclined light source scans or passes may be used. A scanning device 102 (see FIG. 5) with a 45° (forty-five degree) light source 106a (see FIG. 5) may be used to image the entire thickness of the composite laminate 28 (see FIG. 5). Alternatively, if the scanning device 102 (see FIG. 5) has two off-axis inclined light sources 106 (see FIG. 5), a layer of tape may be placed over one off-axis inclined light source 106 (see FIG. 5), and the scanning device 102 (see FIG. 5) may be used to image the entire thickness of the composite laminate 28 (see FIG. 5). Multiple composite laminates 28 (see FIG. 5) may be imaged simultaneously, and may be constrained only by the size of the scanning device 102 (see FIG. 5).

Thus, disclosed embodiments of the method 66 (see FIG. 4A), the method 80 (see FIG. 4B) and the system 90 (see FIG. 5) may be polished much faster than the polishing procedures required with known methods and systems, may require only one single cut of the composite laminate 28 sample rather than two, may not require mounting in order to be polished, may not require composite imaging, and may significantly reduce the difficulty of visual methods of ply orientation determination.

Many modifications and other embodiments of the disclosure will come to mind to one skilled in the art to which this disclosure pertains having the benefit of the teachings presented in the foregoing descriptions and the associated drawings. The embodiments described herein are meant to be illustrative and are not intended to be limiting or exhaustive. Although specific terms are employed herein, they are used in a generic and descriptive sense only and not for purposes of limitation.

What is claimed is:

1. A method for determining and verifying ply orientation of an entire thickness of a composite laminate, the method comprising the steps of:

preparing an edge of the composite laminate comprised of a plurality of plies, to obtain a prepared edge that provides visibility of the plurality of plies at the prepared edge, in scanned images of the prepared edge, after the prepared edge has been scanned, and wherein preparing the edge comprises one or more of, smoothing, polishing, abrading, finishing, and cleaning the edge of the composite laminate;

performing a first scan of the prepared edge and the entire thickness of the composite laminate using an off-axis inclined light source directing light at a first acute angle to a first area on the prepared edge to produce a first scanned image, the thickness of the composite laminate oriented transverse to a light source travel path of the off-axis inclined light source and oriented perpendicular to sides of the composite laminate;

rotating an orientation of the off-axis inclined light source relative to the prepared edge, such that the off-axis inclined light source directs light at a second acute angle symmetrically opposite the first acute angle;

performing a second scan of the prepared edge and the entire thickness of the composite laminate using the off-axis inclined light source directing light at the symmetrically opposite second acute angle to the first area on the prepared edge to produce a second scanned image; inclined light source and oriented perpendicular to sides of the composite laminate;

comparing the first scanned image and the second scanned image to determine a ply orientation of each ply of the plurality of plies of the composite laminate, wherein the ply orientation is determined based on light source reflections of the off-axis inclined light source; and, verifying the ply orientation of the composite laminate against a baseline ply orientation of a baseline composite laminate.

2. The method of claim 1 wherein the steps of performing the first scan, rotating the orientation of the off-axis inclined light source, and performing the second scan, comprise using the off-axis inclined light source comprising one of, a fluorescent lamp, a cold cathode fluorescent lamp, a xenon lamp, and a light-emitting diode (LED) light.

3. The method of claim 1 wherein the steps of performing the first scan of the prepared edge and the entire thickness of the composite laminate and performing the second scan of the prepared edge and the entire thickness of the composite laminate comprise using a scanning device having a 45° (forty-five degree) light source.

4. The method of claim 1 wherein the steps of performing the first scan of the prepared edge and the entire thickness of the composite laminate and performing the second scan of the prepared edge and the entire thickness of the composite laminate comprise using a scanning device having an optical resolution of 1200 dpi (dots per inch) or greater.

5. The method of claim 1 wherein the step of rotating the orientation of the off-axis inclined light source relative to the prepared edge comprises rotating the orientation of the off-axis inclined light source 180 degrees relative to the prepared edge.

6. The method of claim 1 wherein the step of comparing the first scanned image and the second scanned image to determine the ply orientation comprises using a manual visual comparison of the light source reflections of the first scanned image and the second scanned image.

7. The method of claim 1 wherein the step of comparing the first scanned image and the second scanned image to determine the ply orientation comprises using an automated comparison with a process software to compare the light source reflections of the first scanned image and the second scanned image.

8. The method of claim 1 wherein the step of comparing the first scanned image and the second scanned image to determine the ply orientation comprises determining the ply orientation based on light source reflections comprising bright/dark transition reflections in +/−45° (plus/minus forty-five) degree to a cross-section surface of the prepared edge, dark reflections for plies normal to the cross-section surface of the prepared edge, and bright reflections for plies parallel to the cross-section surface of the prepared edge.

9. The method of claim 1 wherein the step of verifying the ply orientation of the composite laminate comprises verifying that a plurality of plies of the composite laminate are laid up correctly as intended by design.

10. The method of claim 1 further comprising prior to the verifying step, the step of preparing a baseline matrix comprising the baseline ply orientation of a plurality of baseline plies of the baseline composite laminate.

11. A method for determining and verifying ply orientation of an entire thickness of a composite laminate of an aircraft composite structure, the method comprising the steps of:

preparing an edge of the composite laminate comprised of a plurality of plies, to obtain a prepared edge that provides visibility of the plurality of plies at the prepared edge, in scanned images of the prepared edge, after the prepared edge has been scanned, and wherein preparing the edge comprises one or more of, smoothing, polishing, abrading, finishing, and cleaning the edge of the composite laminate;

performing with a scanning device having at least one off-axis inclined light source a first scan of the prepared edge and the entire thickness of the composite laminate using the at least one off-axis inclined light source to direct light at a first acute angle to a first area on the prepared edge to produce a first scanned image, the thickness of the composite laminate oriented transverse to a light source travel path of the off-axis inclined light source and oriented perpendicular to sides of the composite laminate;

rotating 180 degrees an orientation of the at least one off-axis inclined light source relative to the prepared edge, such that the off-axis inclined light source directs light at a second acute angle symmetrically opposite the first acute angle;

performing with the scanning device a second scan of the prepared edge and the entire thickness of the composite laminate using the at least one off-axis inclined light source to direct light at the symmetrically opposite second acute angle to the first area on the prepared edge to produce a second scanned image;

transferring the first scanned image and the second scanned image from the scanning device to a processing device for processing;

comparing the first scanned image and the second scanned image to determine a ply orientation of each ply of the plurality of plies of the composite laminate, wherein the ply orientation is determined based on light source reflections of the at least one off-axis inclined light source;

preparing a baseline matrix comprising a baseline ply orientation of a baseline composite laminate of the aircraft composite structure; and, verifying the ply orientation of the composite laminate against the baseline ply orientation of the baseline matrix.

12. The method of claim 11 wherein the steps of performing the first scan of the prepared edge and the entire thickness of the composite laminate and performing the second scan of the prepared edge and the entire thickness of the composite laminate comprise performing with the scanning device having a 45° (forty-five degree) light source and an optical resolution of 1200 dpi (dots per inch) or greater.

13. The method of claim 11 wherein the step of comparing the first scanned image and the second scanned image to determine the ply orientation comprises using at least one of a manual visual comparison and an automated comparison with a process software, of the light source reflections of the first scanned image and the second scanned image.

14. The method of claim 11 wherein the step of comparing the first scanned image and the second scanned image to determine the ply orientation comprises determining the ply orientation based on light source reflections comprising bright/dark transition reflections in +/−45° (plus/minus forty-five) degree plies to a cross-section surface of the prepared edge, dark reflections for plies normal to the cross-section surface of the prepared edge, and bright reflections for plies parallel to the cross-section surface of the prepared edge.

15. A system for determining and verifying ply orientation of an entire thickness of a composite laminate, the system comprising:
a composite laminate that is cured and comprises at least one prepared edge and a plurality of plies, each ply having a ply orientation, and the at least one prepared edge providing visibility of the plurality of plies at the prepared edge, in scanned images of the prepared edge, after the prepared edge has been scanned, and the prepared edge being prepared by one or more of, smoothing, polishing, abrading, finishing, and cleaning; and
a scanning assembly comprising:
a scanning device having at least one off-axis inclined light source configured to direct light at a first acute angle to a first area on the prepared edge and the entire thickness of the composite laminate to illuminate and capture a first scanned image, the thickness of the composite laminate oriented transverse to a light source travel path of the off-axis inclined light source and oriented perpendicular to sides of the composite laminate, and further configured to reorient the direction of the off-axis light source to a second acute angle symmetrically opposite the first acute angle, to direct light at a symmetrically opposite second acute angle to the first area on the prepared edge and the entire thickness to illuminate and capture a second scanned image;
a processing device coupled to the scanning device, the processing device configured to receive and process the first scanned image and the second scanned image from the scanning device; and
a baseline matrix comprising a baseline ply orientation of a baseline composite laminate,
wherein the system provides a ply orientation determination of each ply of the composite laminate based on light source reflections of the at least one off-axis inclined light source and a comparison of the first scanned image and the second scanned image, and further wherein the system provides a ply orientation verification of the composite laminate using the baseline matrix.

16. The system of claim 15 wherein the composite laminate is a fiber-reinforced composite laminate comprised of continuous fibers.

17. The system of claim 15 wherein the scanning device has an optical resolution of 1200 dpi (dots per inch) or greater.

18. The system of claim 15 wherein the at least one off-axis inclined light source comprises a light source oriented at 45° (forty-five degree) relative to the prepared edge.

19. The system of claim 15 wherein the processing device comprises a computer having process software to process the first scanned image and the second scanned image to enable comparison of the first scanned image and the second scanned image against each other and against the baseline matrix.

20. The system of claim 15 wherein the light source reflections comprise bright/dark transition reflections in +/−45° (plus/minus forty-five degree) plies to a cross-section surface of the prepared edge, dark reflections for plies normal to the cross-section surface of the prepared edge, and bright reflections for plies parallel to the cross-section surface of the prepared edge.

* * * * *